United States Patent
Liu et al.

(10) Patent No.: US 7,304,190 B2
(45) Date of Patent: Dec. 4, 2007

(54) PHOTORESIST COMPOSITIONS COMPRISING DIAMONDOID DERIVATIVES

(75) Inventors: Shenggao Liu, Hercules, CA (US); Jeremy E. Dahl, Palo Alto, CA (US); Robert M. Carlson, Petaluma, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 210 days.

(21) Appl. No.: 11/266,333

(22) Filed: Nov. 4, 2005

(65) Prior Publication Data

US 2006/0057496 A1 Mar. 16, 2006

Related U.S. Application Data

(62) Division of application No. 10/764,407, filed on Jan. 23, 2004.

(60) Provisional application No. 60/508,222, filed on Oct. 1, 2003.

(51) Int. Cl.
C07C 35/22 (2006.01)
(52) U.S. Cl. .................................................. 568/818
(58) Field of Classification Search ................... None
See application file for complete search history.

(56) References Cited

U.S. PATENT DOCUMENTS

| | | |
|---|---|---|
| 5,166,313 A | 11/1992 | Archibald et al. |
| 5,268,513 A | 12/1993 | Shen et al. |
| 5,399,647 A | 3/1995 | Nozaki |
| 5,430,193 A | 7/1995 | Shen |
| 5,621,019 A | 4/1997 | Nakano et al. |
| 5,665,518 A | 9/1997 | Maeda et al. |
| 5,691,111 A | 11/1997 | Iwasa et al. |
| 5,756,850 A | 5/1998 | Iwasa et al. |
| 5,929,271 A | 7/1999 | Hada et al. |
| 6,013,416 A | 1/2000 | Nozaki et al. |
| 6,042,991 A | 3/2000 | Aoai et al. |
| 6,071,670 A | 6/2000 | Ushirogouchi et al. |
| 6,077,644 A | 6/2000 | Hada et al. |
| 6,087,063 A | 7/2000 | Hada et al. |
| 6,103,445 A | 8/2000 | Wilson et al. |
| 6,124,074 A | 9/2000 | Varanasi et al. |
| 6,136,501 A | 10/2000 | Trefonas, III et al. |
| 6,200,724 B1 | 3/2001 | Namiki et al. |
| 6,200,728 B1 | 3/2001 | Cameron et al. |
| 6,225,019 B1 | 5/2001 | Matsuda et al. |
| 6,225,476 B1 | 5/2001 | Hada et al. |
| 6,238,842 B1 | 5/2001 | Sato et al. |
| 6,245,485 B1 | 6/2001 | Aoai et al. |
| 6,251,569 B1 | 6/2001 | Angelopoulos et al. |
| 6,268,106 B1 | 7/2001 | Park et al. |
| 6,291,130 B1 | 9/2001 | Kodama et al. |
| 6,306,554 B1 | 10/2001 | Barclay et al. |
| 6,313,327 B1 | 11/2001 | Seo et al. |
| 6,344,590 B1 | 2/2002 | Nakano et al. |
| 6,380,270 B1 | 4/2002 | Yates |
| 6,383,713 B1 | 5/2002 | Uetani et al. |
| 6,388,101 B1 | 5/2002 | Hada et al. |
| 6,391,520 B1 | 5/2002 | Nakano et al. |
| 6,403,280 B1 | 6/2002 | Yamahara et al. |
| 6,403,823 B2 | 6/2002 | Hasegawa et al. |
| 6,416,925 B1 | 7/2002 | Aoai et al. |
| 6,440,636 B1 | 8/2002 | Ushirogouchi et al. |
| 6,462,158 B1 | 10/2002 | Miwa et al. |
| 6,465,137 B2 | 10/2002 | Watanabe et al. |
| 6,479,211 B1 | 11/2002 | Sato et al. |
| 6,486,330 B1 | 11/2002 | Nakano |
| 6,489,082 B1 | 12/2002 | Hattori et al. |
| 6,492,086 B1 | 12/2002 | Barclay et al. |
| 6,498,226 B2 | 12/2002 | Cheng et al. |
| 6,517,991 B1 | 2/2003 | Kodama et al. |
| 6,548,221 B2 | 4/2003 | Uetani et al. |
| 6,552,143 B2 | 4/2003 | Funaki et al. |
| 6,555,289 B2 | 4/2003 | Sasaki et al. |
| 6,562,554 B1 | 5/2003 | Varanasi et al. |
| 6,566,038 B2 | 5/2003 | Nishi et al. |
| 2001/0026901 A1 | 10/2001 | Maeda et al. |

(Continued)

FOREIGN PATENT DOCUMENTS

| | | |
|---|---|---|
| WO | WO 92/13909 | 8/1992 |
| WO | WO 02/057201 A2 | 7/2002 |
| WO | WO 02/058139 | 7/2002 |
| WO | WO 02/088077 | 11/2002 |

OTHER PUBLICATIONS

Liaw, Der-Jang, "Synthesis and characterization of new polyamides and polyimides prepared from 2,2-bis[4-(4-aminophenoxy)phenyl]adamantane," *Macromol. Chem. Phys.* 200. No. 6, pp. 1326-1332 (1999).

Nozaki, Koji et al., "High-Performance Resist Materials for ArF Excimer Laser and Electron Beam Lithography," *FUJITSU Sci Tech. J.*, 38, 1, pp. 3-12 (Jun. 2002).

Padmanaban, Munirathna, et al., "Etch Properties of 193nm Resists: Issues and Approaches," *Journal of Photopolymer Science and Technology*, vol. 15, No. 3 (2002), pp. 521-528.

Padmanaban, Munirathna, et al., "Layer-Specific Resists for 193nm Lithography," *Journal of Photopolymer Science and Technology*, vol. 13, No. 4 (2000) pp. 607-616.

(Continued)

*Primary Examiner*—Yvonne Eyler
*Assistant Examiner*—M Louisa Lao
(74) *Attorney, Agent, or Firm*—E. Joseph Gess, Esq.

(57) ABSTRACT

Novel positive-working photoresist compositions are disclosed. The monomers of the base resin of the resist contain diamondoid-containing pendant groups higher than adamantane in the polymantane series; for example, diamantane, triamantane, tetramantane, pentamantane, hexamantane, etc. The diamondoid-containing pendant group may have hydrophilic-enhancing substituents such as a hydroxyl group, and may contain a lactone group. Advantages of the present compositions include enhanced resolution, sensitivity, and adhesion to the substrate.

10 Claims, 26 Drawing Sheets

U.S. PATENT DOCUMENTS

| | | |
|---|---|---|
| 2002/0016414 A1 | 2/2002 | Lau et al. |
| 2002/0016516 A1 | 2/2002 | Nakano et al. |
| 2002/0037472 A1 | 3/2002 | Zampini et al. |
| 2002/0048720 A1 | 4/2002 | Sasaki et al. |
| 2002/0048725 A1 | 4/2002 | Oshima |
| 2002/0064727 A1 | 5/2002 | Sato |
| 2002/0076543 A1 | 6/2002 | Sikonia |
| 2002/0099147 A1 | 7/2002 | Yoshida et al. |
| 2002/0120090 A1 | 8/2002 | Cheng et al. |
| 2002/0123010 A1 | 9/2002 | Angelopoulos et al. |
| 2002/0130407 A1 | 9/2002 | Dahl et al. |
| 2002/0132181 A1 | 9/2002 | Nishimura et al. |
| 2002/0134301 A1 | 9/2002 | Dahl et al. |
| 2002/0136987 A1 | 9/2002 | Oshima |
| 2002/0137976 A1 | 9/2002 | Dahl et al. |
| 2002/0143217 A1 | 10/2002 | Dahl et al. |
| 2002/0143218 A1 | 10/2002 | Dahl et al. |
| 2002/0147373 A1 | 10/2002 | Dahl et al. |
| 2002/0169266 A1 | 11/2002 | Funaki et al. |
| 2002/0177743 A1 | 11/2002 | Dahl et al. |
| 2002/0182360 A1 | 12/2002 | Koshiyama et al. |
| 2002/0182534 A1 | 12/2002 | Varanasi et al. |
| 2002/0187420 A1 | 12/2002 | Barclay et al. |
| 2002/0188163 A1 | 12/2002 | Dahl et al. |
| 2002/0193648 A1 | 12/2002 | Dahl et al. |
| 2003/0008241 A1 | 1/2003 | Sato et al. |
| 2003/0017415 A1 | 1/2003 | Kodama et al. |
| 2003/0017635 A1 | 1/2003 | Apen et al. |
| 2003/0031789 A1 | 2/2003 | Bedwell et al. |
| 2003/0031949 A1 | 2/2003 | Barclay et al. |
| 2003/0031950 A1 | 2/2003 | Uenishi et al. |
| 2003/0044717 A1 | 3/2003 | Kodama |
| 2003/0044718 A1 | 3/2003 | Kodama et al. |
| 2003/0059710 A1 | 3/2003 | Inoue |
| 2003/0064327 A1 | 4/2003 | Rottstegge |
| 2003/0068585 A1 | 4/2003 | Rottstegge |
| 2003/0073027 A1 | 4/2003 | Namiki et al. |
| 2003/0077540 A1 | 4/2003 | Kodama et al. |
| 2003/0077543 A1 | 4/2003 | Sato |
| 2003/0102285 A1 | 6/2003 | Nozaki et al. |
| 2003/0105264 A1 | 6/2003 | Bedwell et al. |
| 2003/0108809 A1 | 6/2003 | Sato |
| 2003/0114598 A1 | 6/2003 | Li et al. |
| 2003/0134225 A1 | 7/2003 | Fujimori et al. |
| 2003/0148206 A1 | 8/2003 | Kodama |
| 2003/0148210 A1 | 8/2003 | Funaki et al. |
| 2005/0112494 A1 | 5/2005 | Yao et al. |
| 2005/0147915 A1 | 7/2005 | Dammel |

OTHER PUBLICATIONS

Paniez, P. J., et al., "Thermal Phenomena in Acryllic 193 nm Resists," SPIE Conferences on Advances in Resist Technology and Processing XVI, Santa Clara, CA, *SPIE* vol. 3678 pp. 1352-1363.

Shida, Naomi, "Advanced Materials for 193-nm Resists," *Journal of Photopolymer Science and Technology*, vol. 13, No. 4 (2000) pp. 601-606.

Ushirogouchi, Tohru, et al., "Advanced Materials for 193-nm Resists," In *Advances in Resist Technology and Processing XVII*, Francis M. Houlihan, Editor, Proceedings of SPIE vol. 3999 (2000) pp. 1147-1156.

Williams, Van Zandt, Jr., et al., "Triamantane", *Journal of the American Chemical Society* 88(16):3862-3863 (1966).

Gund, T.M., et al., "The Functionalization of Diamantane (Congressane)", *Tetrahedron Letters* 56:4875-4878 (1970).

Wang, Jane-Jen, et al., "Synthesis and Characterization of New Poly(*N*-1-adamantylmaleimide) and Poly(*N*-1-diamantylmaleimide)", *Journal of Polymer Science: Part A: Polymer Chemistry* 34:3345-3354 (1996).

Cupus, et al., "Congressane", *Journal of the American Chemical Society* 87(4):917-918 (1965).

Ishii, Yasutaka et al., "Hydroxylation of polycyclic alkanes with molecular oxygen catalyzed by N-hydroxyphthalimide (NHPI) combined with transition metal salts", *Tetrahedron Letters* 37(28):4993-4996 (1996).

EP Search Report mailed Dec. 5, 2006 from EP 04 80 9820.

Representative Ways of Generation of Diamondoid Cations ($D^+$)

Representative $S_N1$ Reactions of Diamondoid Carbocations

Representative $S_E2$ Reactions of Diamondoids

PHOTORESIST COMPOSITIONS COMPRISING DIAMONDOID DERIVATIVES

REFERENCE TO RELATED APPLICATIONS

The present application claims the benefit of U.S. Provisional Patent Application No. 60/508,222 filed Oct. 1, 2003. U.S. Provisional Application No. 60/508,222 is hereby incorporated by reference in its entirety.

The present application is a divisional of U.S. Ser. No. 10/764,407, filed on Jan. 23, 2004, hereby incorporated by reference in its entirety.

BACKGROUND OF THE INVENTION

1. Field of the Invention

Embodiments of the present invention are directed in general toward high performance photoresist compositions used in conjunction with eximer laser and electron beam lithography sources. Specifically, the photoresist compositions of the present invention include diamondoid derivatives having polymerizable and hydrophilic-enhancing functionalities. The diamondoids of the present invention include lower diamondoids such as adamantane, diamantane, and triamantane, as well as the diamondoids tetramantane, pentamantanes, and higher compounds.

2. State of the Art

Increasing demands for devices with higher circuit densities have led to the use of shorter wavelength light sources in optical lithography. KrF (krypton fluoride) excimer laser lithography operating at a wavelength of 248 nm has been used for the production of devices having feature sizes ranging from 0.25 to 0.13 microns. Rapid advances in the miniaturization of microelectronic devices, and demands for devices with increasingly greater circuit densities, are requiring the development of new, imageable polymeric photoresist materials to be used with ArF (argon fluoride) excimer laser lithography at 193 nm, and there is a need on the horizon for resist materials which can operate in the extreme ultraviolet and soft x-ray regim. According to *The National Technology Roadmap for Semiconductors*, (Semiconductor Industry Association, San Jose, Calif., 1997), the next most likely candidate is an $F_2$ source operating at 157 nm.

Conventional g-line (436 nm) and i-line (365 nm) photoresists are well-balanced in terms of high-resolution, high sensitivity, and good dry etch resistance, but they typically comprise a novolac base resin and a diazonaphthoquinone PAC (photoactive compound), both of which contain a phenolic moiety that absorbs light having wavelengths below about 365 nm. Thus, the phenolic based resists cannot be used in these shorter wavelengths regimes, such as those found in ArF lithography, because they are completely opaque at 193 nm. The incident radiation cannot penetrate through the full thickness of the resist. This is a significant issue at 248 nm (KrF), which is the wavelength used for 0.25 micron and 0.18 micron generation devices.

Photoresists are materials used to transfer an image onto a substrate. A layer of the photoresist (or "resist") is formed on a substrate, and then exposed through a mask to a source of radiation. The mask has some regions that are opaque, and some regions that are transparent to the radiation. The portions of the photoresist that are exposed to the radiation undergo a chemical transformation such that the pattern of the mask is transferred to the photoresist layer, which after development provides a relief image that can be used to selectively process the underlying substrate.

In general, a photoresist composition comprises at least a resin binder and a photoactive agent. The "chemically amplified" resists in use today were developed for the formation of sub-micron images and other high performance applications. They may be either positive or negative acting. In the case of a positive acting resist, the regions that are exposed to the radiation become more soluble in the developer, while those areas that are not exposed remain comparatively less soluble in the developer. Cationic initiators are used to induce cleavage of certain "blocking groups" pendant from the photoresist binder resin, or cleavage of certain groups that comprise a photoresist binder backbone. Upon cleavage of the blocking group through exposure of a layer of photoresist to light, a base soluble functional group is formed, such as a carboxylic acid or an imide, which results in a different solubility in the developer for the exposed and unexposed regions of the resist layer.

As taught by J. D. Plummer et al., in "Silicon VLSI Technology" (Prentice Hall, Upper Saddle River, N.J., 2000), pp. 221-226, deep ultraviolet (DUV) resists in use today are not modified novolac resists. Deep ultraviolet (DUV) photoresist materials in use today are based on chemistry that makes use of a phenomenon called "chemical amplification." Conventional resist materials that were designed to operate at 365 nm and 248 nm achieved quantum efficiencies of about 0.3, meaning that about 30 percent of the incoming photons interacted with the photoactive compound to expose the resist.

DUV resists, according to Plummer, work on a different principle that is illustrated in FIG. 1. Referring to FIG. 1, incoming photons react with a photo-acid generator (PAG) 101, creating an acid molecule 102. Acid molecules 102 act as catalysts during a subsequent resistant bake to change the properties of the resist in the exposed region. The photo-acid generator 101 initiates a chemical reaction that makes the resist soluble in a developer in a subsequent developing step that occurs after exposure to the radiation. The reactions are catalytic and the acid molecule 102 is regenerated after each chemical reaction and may therefore participate in tens or even hundreds of further reactions. This is what allows the overall quantum efficiency in a chemically amplified resist to be much larger than 1, and is responsible for improving the sensitivity of a chemically amplified resist from the previous values of about 100 mJ cm$^{-2}$ for conventional diazonaphthoquinones to the current values of about 20-40 for the new chemically amplified the ultraviolet photoresists.

The principle of a chemically amplified photoresist is illustrated in FIG. 1. Referring again to FIG. 1, photoresists of the present intention included in general a photo-acid generator 101 and a blocked or protected polymer 103 which is insoluble in the developer because of attached molecules 104 (labeled additionally "INSOL" in FIG. 1). Incident deep ultraviolet photons interact with the photo-acid generator 101 to create an acid molecule 102. The spatial pattern of the acid molecules 102 within the resist create a "stored," or latent image of the mask pattern. After exposure, the substrate undergoing processing is baked at a temperature of about 120 degrees C. in a process called post exposure bake (PEB). The heat from the post exposure bake provides the energy needed for the reaction between the acid molecules 102 and the insoluble pendant groups 104 where the reaction is to take place. The heat from the post exposure bake provides the energy needed for the reaction between acid molecules 102 and the insoluble pendant groups 104 attached to main polymer chain 103; the heat from the post exposure bake also provides diffusion mobility for the acid molecules 102 to seek out unreacted pendant groups 104, the essence of the catalytic nature of this reaction.

During the post exposure bake, the insoluble pendant groups 104 are either converted to soluble pendant groups 105, or cleaved from the polymer chain 103. In either case, the insoluble, blocked polymer is converted to an unblocked polymer as soluble in an aqueous alkaline developer.

The polymers that comprise the chain 103 may comprise such polymers as polyamides, polyimides, polyesters, and polycarbonates since these are easily processed, mechanically strong, and thermally stable, and thus have become important materials in the microelectronics industry. Introduction of polycyclic hydrocarbon substituents, including alicyclic rings and other caged hydrocarbons, have been shown to impart greater solubility and enhanced rigidity, improving the mechanical and thermal properties of the resulting polymers. Previous studies have involved the introduction of adamantyl groups into 193 nm resists, but to the applicant's knowledge, there have been no previous attempts to incorporate any diamondoid compound higher than adamantane into the base resin structure. These composition may incorporate lower diamondoids such as diamantane and/or triamantane into the resist structure, or they may include diamondoids such as tetramantane and higher.

In many instances, the use of photoacid generators that produce weaker photoacids and resists compositions that require lower post exposure bake (PEB) temperatures, such as 110° C. or less, would represent a significant advantage. For example, if the desired deprotection chemistry could be carried out with a weaker acid, a wider range of photoacid generators could potentially be employed. Moreover, the industry continually seeks use of lowered post exposure bake temperatures because of uniformity considerations.

Thus, it would be advantageous to have new photoresist compositions, particularly positive acting photoresist compositions, that may be effectively imaged in the sub-200 nm wavelength region, such as 193 nm and 157 nm. It is also desirable to provide photoresist compositions that employ photoacid generators.

Adamantane, the smallest member of the family of diamondoid compounds, is a highly condensed, exceptionally stable hydrocarbon compound. Adamantane and a range of adamantyl derivatives have been commercially available for years. This has made adamantane a regular substituent in a wide variety of families of chemical structures when a large, stable, bulky hydrocarbon moiety is desired. Adamantyl groups are found in polymers and are currently employed as constituents of positive photoresist materials.

Diamantane is also a highly condensed hydrocarbon compound. It is made up of two face-fused adamantane units. It can be synthesized but also occurs naturally in petroleum and can be isolated from various deep well hydrocarbon streams such as natural gas streams. A number of diamantane derivatives have been reported in the literature including a variety of mono and poly halides, mono- and dihydroxy materials, mono- and dicarboxylic acid derivatives, mono- and dialkynyls, and mono- and diamines. In addition, there are a number of diamantane-containing polymers in the literature but generally these materials appear to link the diamantane into the polymer through two or more links such that the diamantane forms an integral part of the polymer backbone.

We now desire to provide a family of derivatives of diamantane that can form polymers having pendant diamantyl groups. In addition, these derivative can contain additional functionality to impart desirable properties to the polymers they form.

SUMMARY OF THE INVENTION

Embodiments of the present invention are directed to positive working photoresist compositions useable at lithography wavelengths less than about 200 nm, such as the 193 nm wavelength from an ArF eximer laser, a 157 nm $F_2$ light source, or e-beam excitation. The base resins of the present resist compositions contain acid-cleavable, pendant diamondoid groups that are generally higher in the polymantane series than adamantane. The diamondoid pendant groups have substituents that increase the hydrophilic nature of the diamondoids, thereby rendering them more soluble in an alkali developer, and consequently enhancing their ability to resolve fine feature sizes.

Embodiments of the present invention specifically include polymerizable diamantyl monomers having the formula Pg-D-(R)$_n$, wherein D is a diamantyl nucleus; Pg is a polymerizable group covalently bonded to a carbon of the diamantyl nucleus; n is an integer ranging from 1 to 6, inclusive; at least one of the R's is a hydrophilic-enhancing moiety; and each of the remaining R's is independently selected from the group consisting of hydrogen and a hydrophilic-enhancing moiety. The hydrophilic-enhancing moietyies of these diamantyl monomers may be selected from the group consisting of a hydroxyl group —OH, a carboxylic group —COOH, an alkoxy group —OCH$_3$ or —OC$_2$H$_5$, a keto group —C(O)—, and —OC(O)—OCH$_3$ or —OC(O)—OC$_2$H$_5$.

Other embodiments of the present invention provide for triamantyl monomers having polymerizable groups and hydrophilic-enhancing moities similar to those for diamantyl monomers discussed above, as well as diamondoid-containing monomers with polymerizable groups and hydrophilic-enhancing moities, wherein the diamondoid portion of the diamondoid-containing monomer is selected from the group consisting of tetramantane, pentamantane, hexamantane, heptamantane, octamantane, nonamantane, decamantane, and undecamantane.

Other embodiments of the present invention provide for methods of forming a layer of patterned photoresist on the surface of a substrate, the method comprising the steps of:

a) depositing on the surface of the substrate a layer comprising the above mentionned diamantyl, triamantyl, and higher diamondoid containing monomers having polymerizable groups and hydrophilic-enhancing moieties, b) polymerizing the deposited monomers to yield a polymerized layer comprising a photo-labile polymer on the surface of the substrate; and c) exposing selected regions of the polymerized layer to an electromagnetic beam, thereby modifying the photo-labile polymer in those regions exposed to the electromagnetic beam to yield a selectively modified layer.

In another embodiment, the base resin of the resist may be represented by the general formula:

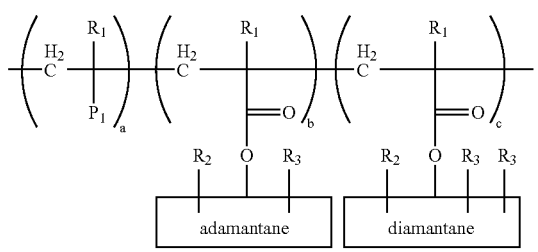

wherein $R_1$ is selected from the group consisting of —H and —$CH_3$;

$R_2$ is selected from the group consisting of —H, an alkyl group having from 1 to 4 carbon atoms, and an alkoxy group having from 1 to 4 carbon atoms;

$R_3$ is —H, or a hydrophilic-enhancing moiety selected from the group consisting of a hydroxyl group —OH, a keto group, carboxylic acid group —COOH, and alkoxy group —$OR_4$, and —$OC(O)OR_4$;

$R_4$ is —$CH_3$ or —$C_2H_5$;

a is 0.25 to 0.75;

b+c=1−a;

c is greater than zero; and $P_1$ is a non-diamondoid, acid-cleavable pendant group.

According to other embodiments of the present invention, the diamondoid pendant groups of the base resin may contain lactone groups, and they may be linked to the main polymer chain by more than one ester linking group, thereby providing multiple sites on which the photo-generated acid can react. This has advantages of allowing either weaker acids, lower post exposure bake temperatures, and a greater variety of photo-acid generators from which to choose. The diamondoid pendant groups may contain hetero atoms in addition to the oxygen atom of a lactone group. The hetero atoms may be selected from the group of O, N, B, S, and/or P. Block co-polymers are also contemplated.

BRIEF DESCRIPTION OF THE DRAWINGS

This invention will be further described with reference being made to the accompanying drawings in which.

DETAILED DESCRIPTION OF THE INVENTION

Figure 1:
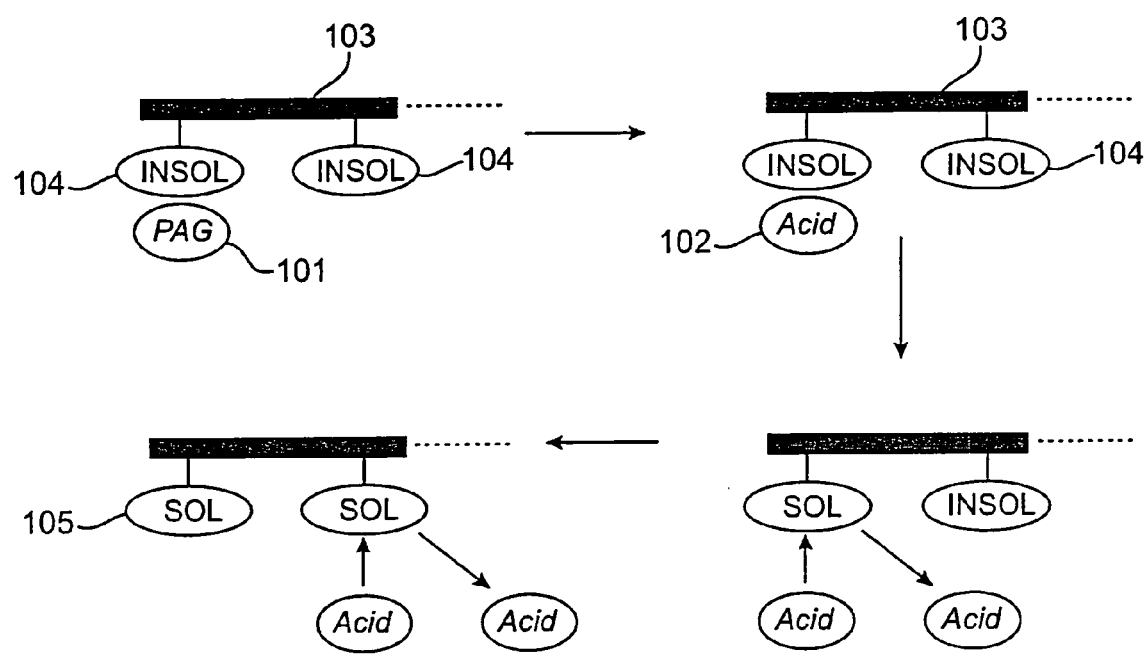
FIG. 1 is a schematic diagram illustrating the manner in which a positive, chemically amplified resist operates, taken from J. D. Plummer et al., in "Silicon VLSI Technology" (Prentice Hall, Upper Saddle River, N.J., 2000), pp. 221-226.
Figure 2:
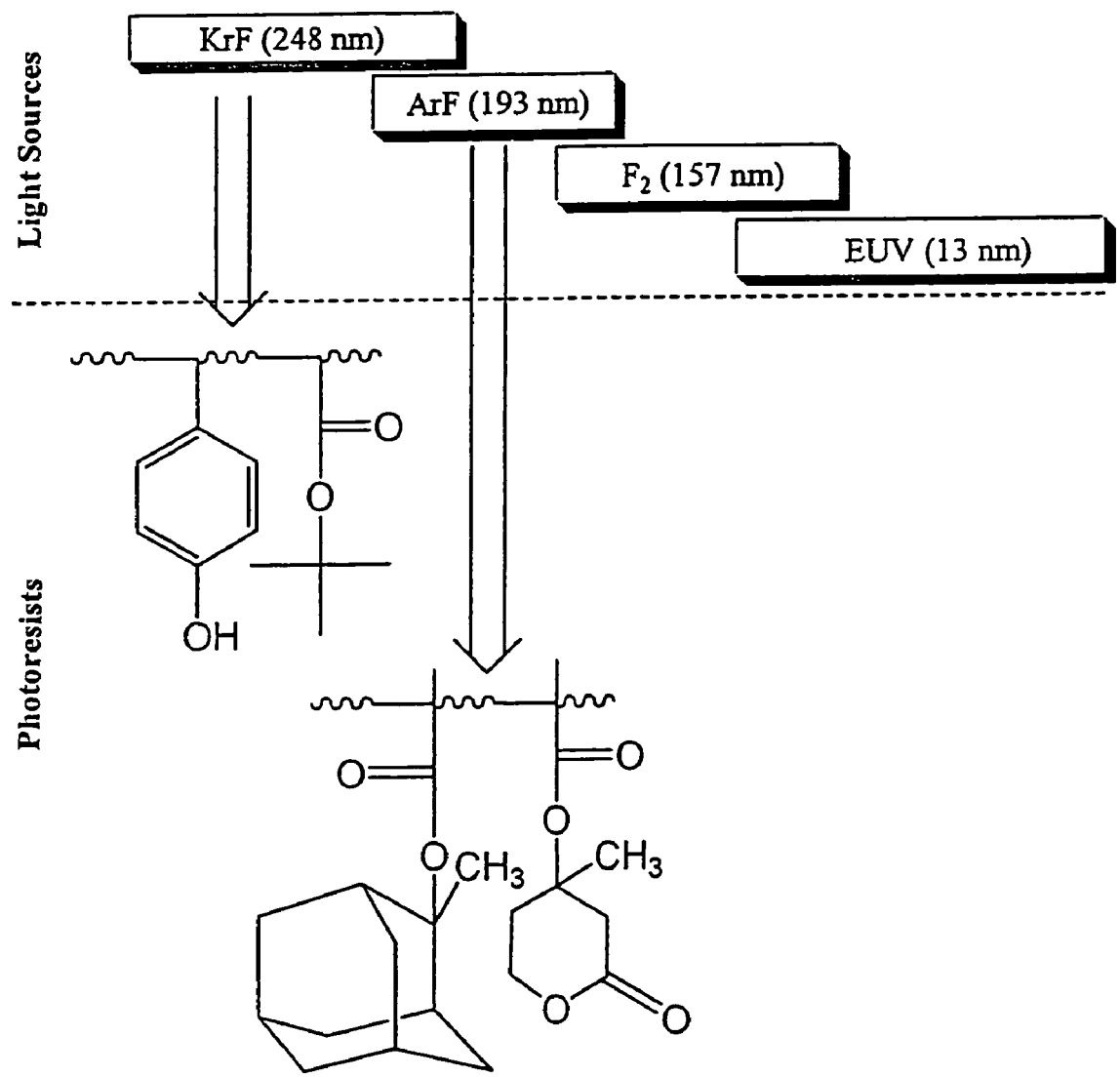
FIG. 2 illustrates an exemplary photoresist that has been used for KrF (248 nm) lithography, and an exemplary photoresist that has been used for ArF (193 nm)
Figure 3:
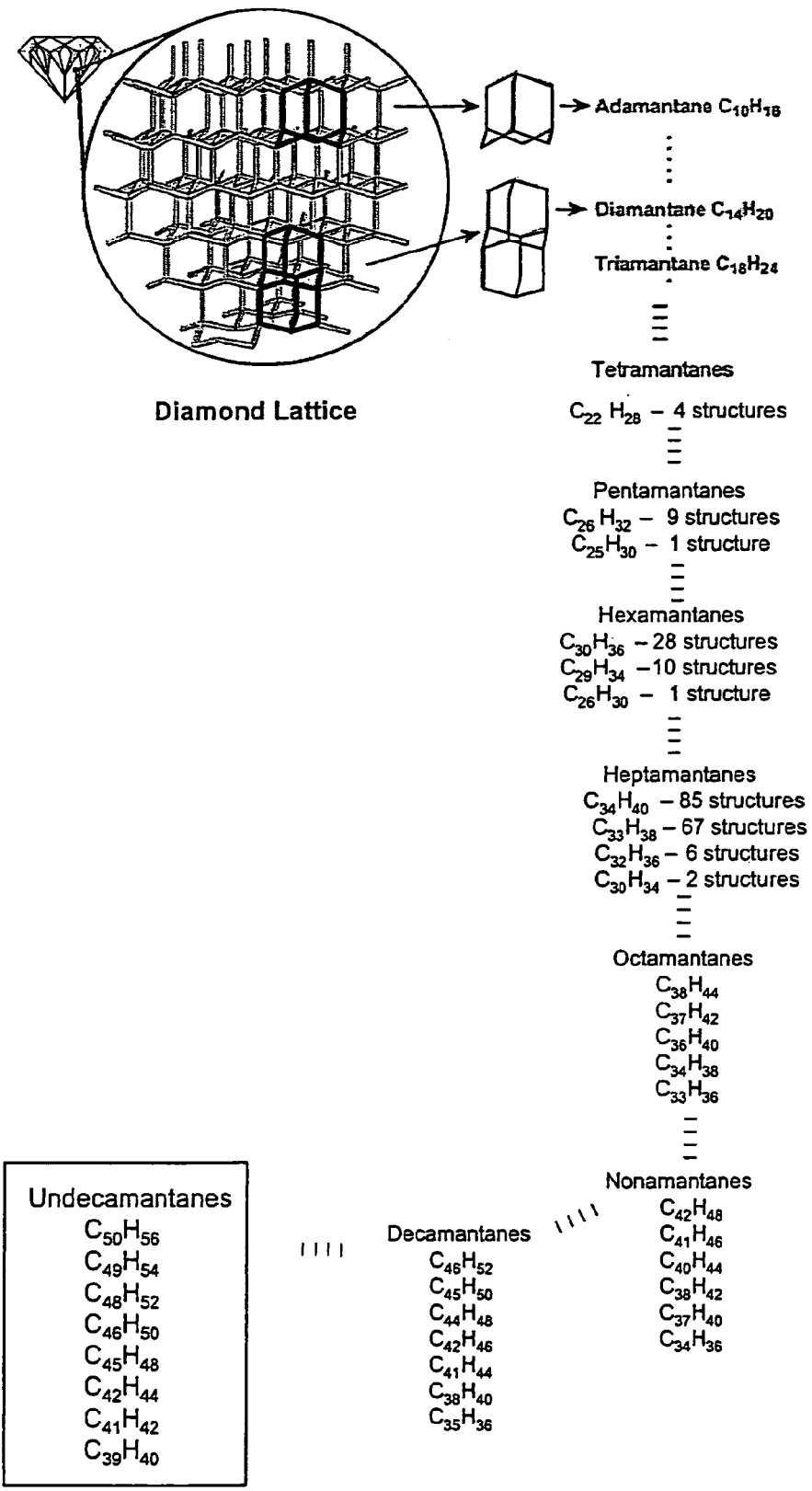
FIG. 3 illustrates the relationship of a diamondoid to the diamond crystal lattice, and enumerates by stoichiometric formula many of the diamondoids available.
Figure 4:
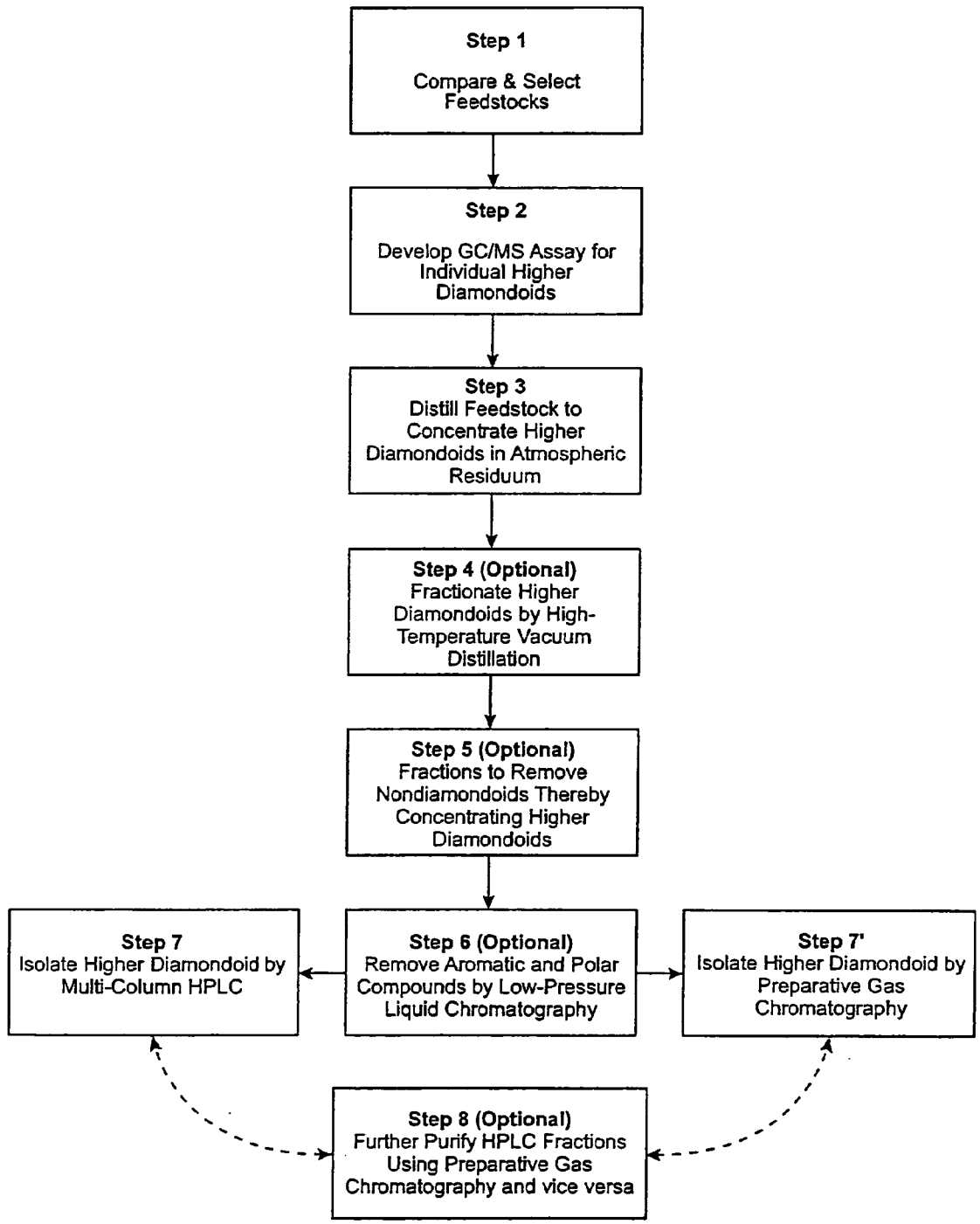
FIG. 4 shows an exemplary process flow for isolating diamondoids from petroleum.

Embodiments of the present invention include diamondoids as pendant groups of the base resin of a positive photoresist composition. The present disclosure will be organized in the following manner: first, the term diamondoids will be defined, followed by a discussion of isolation methods of diamondoids from petroleum feedstocks, the derivatization of those isolated diamondoids, and then polymerization of the derivatized diamondoids into photoresist base resins.

Definition of Diamondoids

The term "diamondoids" refers to substituted and unsubstituted caged compounds of the adamantane series including adamantane, diamantane, triamantane, tetramantane, pentamantane, hexamantane, heptamantane, octamantane, nonamantane, decamantane, undecamantane, and the like, including all isomers and stereoisomers thereof. The compounds have a "diamondoid" topology, which means their carbon atom arrangement is superimposable on a fragment of an FCC diamond lattice. Substituted diamondoids comprise from 1 to 10 and preferably 1 to 4 independently-selected alkyl substituents. Diamondoids include "lower diamondoids" and "diamondoids," as these terms are defined herein, as well as mixtures of any combination of lower and diamondoids.

The term "lower diamondoids" refers to adamantane, diamantane and triamantane and any and/or all unsubstituted and substituted derivatives of adamantane, diamantane and triamantane. These lower diamondoid components show no isomers or chirality and are readily synthesized, distinguishing them from "diamondoids."

The term "diamondoids" refers to any and/or all substituted and unsubstituted tetramantane components; to any and/or all substituted and unsubstituted pentamantane components; to any and/or all substituted and unsubstituted hexamantane components; to any and/or all substituted and unsubstituted heptamantane components; to any and/or all substituted and unsubstituted octamantane components; to any and/or all substituted and unsubstituted nonamantane components; to any and/or all substituted and unsubstituted decamantane components; to any and/or all substituted and unsubstituted undecamantane components; as well as mixtures of the above and isomers and stereoisomers of tetramantane, pentamantane, hexamantane, heptamantane, octamantane, nonamantane, decamantane, and undecamantane.

Adamantane chemistry has been reviewed by Fort, Jr. et al. in "Adamantane: Consequences of the Diamondoid Structure," *Chem. Rev.* vol. 64, pp. 277-300 (1964). Adamantane is the smallest member of the diamondoid series and may be thought of as a single cage crystalline subunit. Diamantane contains two subunits, triamantane three, tetramantane four, and so on. While there is only one isomeric form of adamantane, diamantane, and triamantane, there are four different isomers of tetramantane (two of which represent an enantiomeric pair), i.e., four different possible ways of arranging the four adamantane subunits. The number of possible isomers increases non-linearly with each higher member of the diamondoid series, pentamantane, hexamantane, heptamantane, octamantane, nonamantane, decamantane, etc.

Adamantane, which is commercially available, has been studied extensively. The studies have been directed toward a number of areas, such as thermodynamic stability, functionalization, and the properties of adamantane-containing materials. For instance, the following patents discuss materials comprising adamantane subunits: U.S. Pat. No. 3,457,318 teaches the preparation of polymers from alkenyl adamantanes; U.S. Pat. No. 3,832,332 teaches a polyamide polymer forms from alkyladamantane diamine; U.S. Pat. No. 5,017,734 discusses the formation of thermally stable resins from adamantane derivatives; and U.S. Pat. No. 6,235,851 reports the synthesis and polymerization of a variety of adamantane derivatives.

In contrast, the diamondoids, have received comparatively little attention in the scientific literature. McKervay et al. have reported the synthesis of anti-tetramantane in low yields using a laborious, multistep process in "Synthetic Approaches to Large Diamondoid Hydrocarbons," *Tetrahedron*, vol. 36, pp. 971-992 (1980). To the inventor's knowledge, this is the only diamondoid that has been synthesized to date. Lin et al. have suggested the existence of, but did not isolate, tetramantane, pentamantane, and hexamantane in deep petroleum reservoirs in light of mass spectroscopic studies, reported in "Natural Occurrence of Tetramantane ($C_{22}H_{28}$), Pentamantane ($C_{26}H_{32}$) and Hexamantane ($C_{30}H_{36}$) in a Deep Petroleum Reservoir," *Fuel*, vol. 74(10), pp. 1512-1521 (1995). The possible presence of tetramantane and pentamantane in pot material after a distillation of a diamondoid-containing feedstock has been discussed by Chen et al. in U.S. Pat. No. 5,414,189.

The four tetramantane structures are iso-tetramantane [1(2)3], anti-tetramantane [121] and two enantiomers of skew-tetramantane [123], with the bracketed nomenclature for these diamondoids in accordance with a convention established by Balaban et al. in "Systematic Classification and Nomenclature of Diamond Hydrocarbons-I," *Tetrahedron* vol. 34, pp. 3599-3606 (1978). All four tetramantanes have the formula $C_{22}H_{28}$ (molecular weight 292). There are ten possible pentamantanes, nine having the molecular formula $C_{26}H_{32}$ (molecular weight 344) and among these nine, there are three pairs of enantiomers represented generally by [12(1)3], [1234], [1213] with the nine enantiomeric pentamantanes represented by [12(3)4], [1(2,3)4], [1212]. There also exists a pentamantane [1231] represented by the molecular formula $C_{25}H_{30}$ (molecular weight 330).

Hexamantanes exist in thirty-nine possible structures with twenty eight having the molecular formula $C_{30}H_{36}$ (molecular weight 396) and of these, six are symmetrical; ten hexamantanes have the molecular formula $C_{29}H_{34}$ (molecular weight 382) and the remaining hexamantane [12312] has the molecular formula $C_{26}H_{30}$ (molecular weight 342).

Heptamantanes are postulated to exist in 160 possible structures with 85 having the molecular formula $C_3H_{30}$ (molecular weight 448) and of these, seven are achiral, having no enantiomers. Of the remaining heptamantanes 67 have the molecular formula $C_{33}H_{38}$ (molecular weight 434), six have the molecular formula $C_{32}H_{36}$ (molecular weight 420) and the remaining two have the molecular formula $C_{30}H_{34}$ (molecular weight 394).

Octamantanes possess eight of the adamantane subunits and exist with five different molecular weights. Among the octamantanes, 18 have the molecular formula $C_{34}H_{38}$ (molecular weight 446). Octamantanes also have the molecular formula $C_{38}H_4$ (molecular weight 500); $C_{37}H_{42}$ (molecular weight 486); $C_{36}H_{40}$ (molecular weight 472), and $C_{33}H_{36}$ (molecular weight 432).

Nonamantanes exist within six families of different molecular weights having the following molecular formulas: $C_{42}H_{48}$ (molecular weight 552), $C_{41}H_{46}$ (molecular weight 538), $C_{40}H_{44}$ (molecular weight 524, $C_{38}H_{42}$ (molecular weight 498), $C_{37}H_{40}$ (molecular weight 484) and $C_{34}H_{36}$ (molecular weight 444).

Decamantane exists within families of seven different molecular weights. Among the decamantanes, there is a single decamantane having the molecular formula $C_{35}H_{36}$ (molecular weight 456) which is structurally compact in relation to the other decamantanes. The other decamantane families have the molecular formulas: $C_{46}H_{52}$ (molecular weight 604); $C_{45}H_{50}$ (molecular weight 590); $C_{44}H_{48}$ (molecular weight 576); $C_{42}H_{46}$ (molecular weight 550); $C_{41}H_{44}$ (molecular weight 536); and $C_{38}H_{40}$ (molecular weight 496).

Undecamantane exists within families of eight different molecular weights. Among the undecamantanes there are two undecamantanes having the molecular formula $C_{39}H_{40}$ (molecular weight 508) which are structurally compact in relation to the other undecamantanes. The other undecamantane families have the molecular formulas $C_{41}H_{42}$ (molecular weight 534); $C_{42}H_{44}$ (molecular weight 548); $C_{45}H_{48}$ (molecular weight 588); $C_{46}H_{50}$ (molecular weight 602); $C_{48}H_{52}$ (molecular weight 628); $C_{49}H_{54}$ (molecular weight 642); and $C_{50}H_{56}$ (molecular weight 656).

Isolation of Diamondoids from Petroleum Feedstocks

Feedstocks that contain recoverable amounts of diamondoids include, for example, natural gas condensates and refinery streams resulting from cracking, distillation, coking processes, and the like. Particularly preferred feedstocks originate from the Norphlet Formation in the Gulf of Mexico and the LeDuc Formation in Canada.

These feedstocks contain large proportions of lower diamondoids (often as much as about two thirds) and lower but significant amounts of diamondoids (often as much as about 0.3 to 0.5 percent by weight). The processing of such feedstocks to remove non-diamondoids and to separate higher and lower diamondoids (if desired) can be carried out using, by way of example only, size separation techniques such as membranes, molecular sieves, etc., evaporation and thermal separators either under normal or reduced pressures, extractors, electrostatic separators, crystallization, chromatography, well head separators, and the like.

A preferred separation method typically includes distillation of the feedstock. This can remove low-boiling, non-diamondoid components. It can also remove or separate out lower and diamondoid components having a boiling point less than that of the diamondoid(s) selected for isolation. In either instance, the lower cuts will be enriched in lower diamondoids and low boiling point non-diamondoid materials. Distillation can be operated to provide several cuts in the temperature range of interest to provide the initial isolation of the identified diamondoid. The cuts, which are enriched in diamondoids or the diamondoid of interest, are retained and may require further purification. Other methods for the removal of contaminants and further purification of an enriched diamondoid fraction can additionally include the following nonlimiting examples: size separation techniques, evaporation either under normal or reduced pressure, sublimation, crystallization, chromatography, well head separators, flash distillation, fixed and fluid bed reactors, reduced pressure, and the like.

The removal of non-diamondoids may also include a pyrolysis step either prior or subsequent to distillation. Pyrolysis is an effective method to remove hydrocarbonaceous, non-diamondoid components from the feedstock. It is effected by heating the feedstock under vacuum conditions, or in an inert atmosphere, to a temperature of at least about 390° C., and most preferably to a temperature in the range of about 410 to 450° C. Pyrolysis is continued for a sufficient length of time, and at a sufficiently high temperature, to thermally degrade at least about 10 percent by weight of the non-diamondoid components that were in the feed material prior to pyrolysis. More preferably at least about 50 percent by weight, and even more preferably at least 90 percent by weight of the non-diamondoids are thermally degraded.

While pyrolysis is preferred in one embodiment, it is not always necessary to facilitate the recovery, isolation or purification of diamondoids. Other separation methods may allow for the concentration of diamondoids to be sufficiently high given certain feedstocks such that direct purification methods such as chromatography including preparative gas chromatography and high performance liquid chromatography, crystallization, fractional sublimation may be used to isolate diamondoids.

Even after distillation or pyrolysis/distillation, further purification of the material may be desired to provide selected diamondoids for use in the compositions employed in this invention. Such purification techniques include chromatography, crystallization, thermal diffusion techniques, zone refining, progressive recrystallization, size separation, and the like. For instance, in one process, the recovered feedstock is subjected to the following additional procedures: 1) gravity column chromatography using silver nitrate impregnated silica gel; 2) two-column preparative capillary gas chromatography to isolate diamondoids; 3) crystallization to provide crystals of the highly concentrated diamondoids.

An alternative process is to use single or multiple column liquid chromatography, including high performance liquid chromatography, to isolate the diamondoids of interest. As above, multiple columns with different selectivities may be used. Further processing using these methods allow for more refined separations which can lead to a substantially pure component.

Detailed methods for processing feedstocks to obtain diamondoid compositions are set forth in U.S. Provisional Patent Application No. 60/262,842 filed Jan. 19, 2001; U.S. Provisional Patent Application No. 60/300,148 filed Jun. 21, 2001; and U.S. Provisional Patent Application No. 60/307,063 filed Jul. 20, 2001, incorporated by reference herein in their entirety.

Derivatization of Diamondoids

According to the present embodiments, diamondoid pendant groups are derivatized with at least one functional group to allow attachment to the base polymer chain. Preferably these derivatives have the following Formula I:

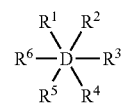

wherein D is a diamondoid nucleus; and, $R^1$, $R^2$, $R^3$, $R^4$, $R^5$ and $R^6$ are each independently selected from a group consisting of hydrogen and covalently bonded functional groups, provided that there is at least one functional group. More preferably the functionalized diamondoids contain either one or two functional groups.

In one aspect, as described in U.S. Ser. No. 10/046,486, in the functionalized diamondoids represented by Formula I, $R^1$, $R^2$, $R^3$, $R^4$, $R^5$ and $R^6$ are preferably independently selected from a group of moieties consisting of —H, —F, —Cl, —Br, —I, —OH, —SH, —NH$_2$, —NHCOCH$_3$, —NHCHO, —CO$_2$H, —CO$_2$R', —COCl, —CHO, —CH$_2$OH, =O, —NO$_2$, —CH=CH$_2$, —C≡CH and —C$_6$H$_5$; where R' is alkyl (preferably ethyl) provided that $R^1$, $R^2$, R3, $R^4$, $R^5$ and $R^6$ are not all hydrogen. Typically one or two of $R^1$-$R^6$ are nonhydrogen moieties and the remaining R's are hydrogens.

Some functionalized diamondoids can be prepared from diamondoid in a single reaction step. These materials are referred to herein as "primary functionalized diamondoids" and include, for example, diamondoids of Formula I wherein the functionalizing groups are halogens, such as -bromos and -chloros, -oxides, -hydroxyls and -nitros as well as other derivatives formed in one reaction from a diamondoid.

In another aspect, the functionalized diamondoids are materials prepared from a primary functionalized diamondoid by one or more subsequent reaction steps. These materials are sometimes referred to herein as "secondary functionalized diamondoids." It will be appreciated that in some cases one primary functionalized diamondoid may be conveniently formed by conversion of another primary material. For example, a poly-bromo material can be formed either by single step bromination or by several repeated brominations. Similarly, a hydroxyl diamondoid can be formed directly from a diamondoid in one step or can be prepared by reaction of a bromo-diamondoid, a diamondoid-oxide or the like. Notwithstanding this, to avoid confusion, the primary materials will not be included here in the representative secondary materials. They will, however, be depicted in various figures showing reactions for forming primary and secondary materials to depict both routes to them.

The functionalized groups available for synthesis of secondary functionalized diamondoids can be selected from a wide range of groups including chloro, bromo, hydroxides, etc. Thus, the following types of secondary materials are merely representatives.

Representative secondary functionalized diamondoid functional groups include fluoro, iodo, thio, sulfonyl halide, sulfonates, alkyl, haloalkyl, alkoxyl, haloalkenyl, alkynyl, haloalkynyl, hydroxyalkyl, heteroaryl, alkylthio, alkoxy; aminoalkyl, aminoalkoxy, aryl, heterocycloalkoxy, cycloalkyloxy, aryloxy, and heteroaryloxy.

Other functional groups that can be present in secondary functionalized diamondoids are represented by the formula —C(O)Z wherein Z is hydrogen, alkyl, halo, haloalkyl, halothio, amino, monosubstituted amino, disubstituted amino, cycloalkyl, aryl, heteroaryl, heterocyclic; by —$CO_2Z$ wherein Z is as defined previously; by —$R^7COZ$ and —$R^7CO_2Z$ wherein $R^7$ is alkylene, aminoalkylene, or haloalkylene and Z is as defined previously; by —$NH_2$; —NHR', —NR'R", and —$N^+R'R''R'''$ wherein R', R", and R''' are independently alkyl, amino, thio, thioalkyl, heteroalkyl, aryl, or heteroaryl; by —$R^8NHCOR^9$ wherein $R^8$ is —$CH_2$, —$OCH_2$, —$NHCH_2$, —$CH_2CH_2$, —$OCH_2CH_2$ and $R^9$ is alkyl, aryl, heteroaryl, aralkyl, or heteroaralkly; and by —$R^{10}CONHR^{11}$ wherein $R^{10}$ is selected from —$CH_2$, —$OCH_2$, —$NHCH_2$, —$CH_2CH_2$, and —$OCH_2CH_2$, and $R^{11}$ is selected from alkyl, aryl, heteroaryl, aralkyl, and heteroaralkyl.

In a further aspect, one or more of the functional groups on the functionalized diamondoids may be of the formulae:

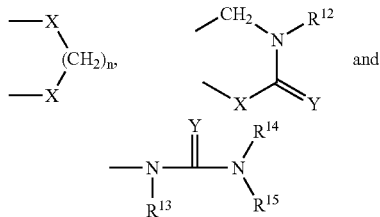

and wherein n is 2 or 3; X is —O—, —S—, or —C(O)—; Y is =O or =S; and $R^{12}$, $R^{13}$, $R^{14}$, and $R^{15}$ are independently hydrogen, alkyl, heteroalkyl, aryl or heteroaryl; =N—Z", wherein Z" is hydrogen, amino, hydroxyl, alkyl,

cyano, cyanoalkyl, cyanoaryl, or cyanoalkylamino.

In a further embodiment, one or more of the functional groups on the functionalized diamondoid is —NHR', —NR'R", —$N^+R'R''R'''$, or —NHQ" wherein R', R", and R''' independently are hydrogen; aryl; heteroaryl with up to 7 ring members; alkyl; alkenyl; or alkynyl, wherein the alkyl, alkenyl and alkynyl residues can be branched, unbranched or cyclized and optionally substituted with halogen, aryl or heteroaryl with up to 7 ring members; or R' and R" together with the nitrogen atom form a heterocyclic group with up to 7 ring members. Q" is thio, thioalkyl, amino, monosubstituted amino, disubstituted amino, or trisubstituted amino with an appropriate counterion such as halogen, hydroxide, sulfate, nitrate, phosphate or other anion.

In still a further embodiment, the functional group on the functionalized diamondoid is —$COOR^{16}$ wherein $R^{16}$ is alkyl, aryl, or aralkyl; —$COR^{17}$, wherein $R^{17}$ is alkyl, aryl, or heteroalkyl, —NHNHO, —$R^{18}NHCOR^{19}$ wherein $R^{18}$ is absent or selected from alkyl, aryl, or aralkyl, $R^{19}$ is hydrogen, alkyl, —$N_2$, aryl, amino, or —$NHR^{20}$ wherein $R^{20}$ is hydrogen, —$SO_2$-aryl, —$SO_2$-alkyl, or —$SO_2$-aralkyl, —$CONHR^{21}$ wherein $R^{21}$ is hydrogen, alkyl, and aralkyl; —$CSNHR^{21}$ wherein $R^{21}$ is as defined above; and —$NR^{22}$—$(CH_2)_n$—$NR^{23}R^{24}$, wherein $R^{22}$, $R^{23}$, $R^{24}$ are independantly selected from hydrogen, alkyl, and aryl, and n is from 1 to 20.

In an additional embodiment, the functional group on the functionalized diamondoid may be —N=C=S; —N=C=O; —R—N=C=O; —R—N=C=S; —N=S=O; or —R—N=S=O wherein R is alkyl; —$PH_2$; —$POX_2$ wherein X is halo; —$PO(OH)_2$; —$OSO_3H$; —$SO_2H$; —SOX wherein X is halo; —$SO_2R$ wherein R is alkyl; —$SO_2OR$ wherein R is alkyl; —$SONR^{26}R^{27}$ wherein $R^{26}$ and $R^{27}$ are independently hydrogen or alkyl; —$N_3$; —OC(O)Cl; or —OC(O)SCl.

In a further aspect, the functionalizing group may form a covalent bond to two or more diamondoids and thus serves as a linking group between the two or more diamondoids. This provides functionalized diamondoids of Formula II:

$$D-L-(D)_n$$

wherein D is a diamondoid nucleus and L is a linking group and n is 1 or more such as 1 to 10 and especially 1 to 4.

In this embodiment, the linking group L may be —N=C—N—

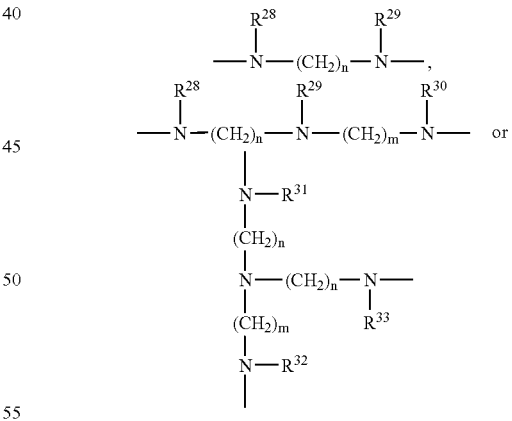

wherein $R^{28}$, $R^{29}$, $R^{30}$, $R^{31}$, $R^{32}$, $R^{33}$ are independently hydrogen or alkyl, and n and m are independently from 2 to 20;

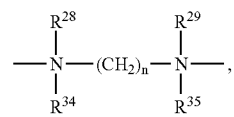

-continued

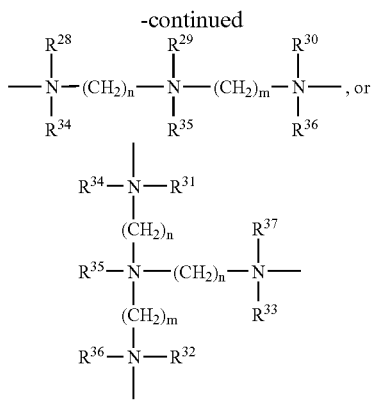

wherein $R^{28}$, $R^{30}$, $R^{31}$, $R^{32}$ and $R^{33}$ are hydrogen or alkyl; $R^{34}$, $R^{35}$, $R^{36}$, and $R^{37}$ are independently absent or hydrogen or alkyl with the proviso that at least one of $R^{34}$, $R^{35}$, $R^{36}$, and $R^{37}$ is present; and n and m are independently from 2 to 20 or the like. The counterion may any acceptable monovalent anion, for example, halogen, hydroxide, sulfate, nitrate, phosphate, and the like.

In another aspect, the present invention relates to functionalized diamondoids of Formula III:

$$R^{38}\text{-D-D-}R^{39}$$

wherein each D is a diamondoid nucleus and $R^{38}$ and $R^{39}$ are substituents on the diamondoid nucleus and are independently hydrogen or a functionalizing group. Preferably the material contains either 1 or 2 functional groups. Preferably $R^{38}$ and $R^{39}$ are halo; cyano; aryl; arylalkoxy; aminoalkyl; or —$COOR^{40}$ wherein $R^{40}$ is hydrogen or alkyl.

In an additional aspect, the present invention provides salts, individual isomers, and mixtures of isomers of diamondoid derivatives of Formulae I, II, and III.

Turning now to the derivatization reaction of diamondoids, there are three different carbons in the diamondoids skeleton: quaternary (4° or C-4), tertiary (3° or C-3), and secondary (2° or C-2) carbons. Of those different carbons, quaternary carbons are impossible to perform any kind of reactions on. Chemical reactions can only take place on those tertiary (3° or C-3) and secondary (20 or C-2) carbons in the diamondoid skeletons. It should be mentioned that some of the tertiary or secondary carbons are equivalent. This means that the derivatives substituted at those equivalent tertiary or secondary carbons are identical.

Figure 5A:
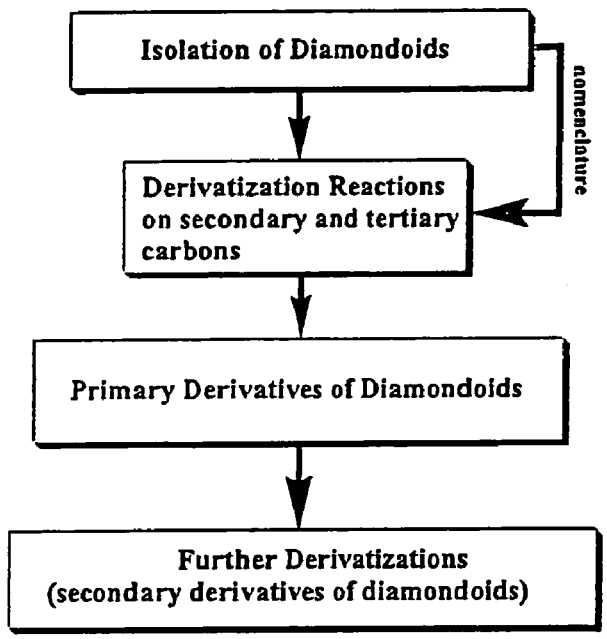
FIG. 5A is a flow chart that illustrates how diamondoids may be derivatized with hydrophilic-enhancing groups and polymerizable groups to form feed monomers, which may then be polymerized to form the base resin of the resist; the base resin is then mixed with a solvent, photoacid generator, and other additives to produce the fully formulated resist.
Figure 5B:
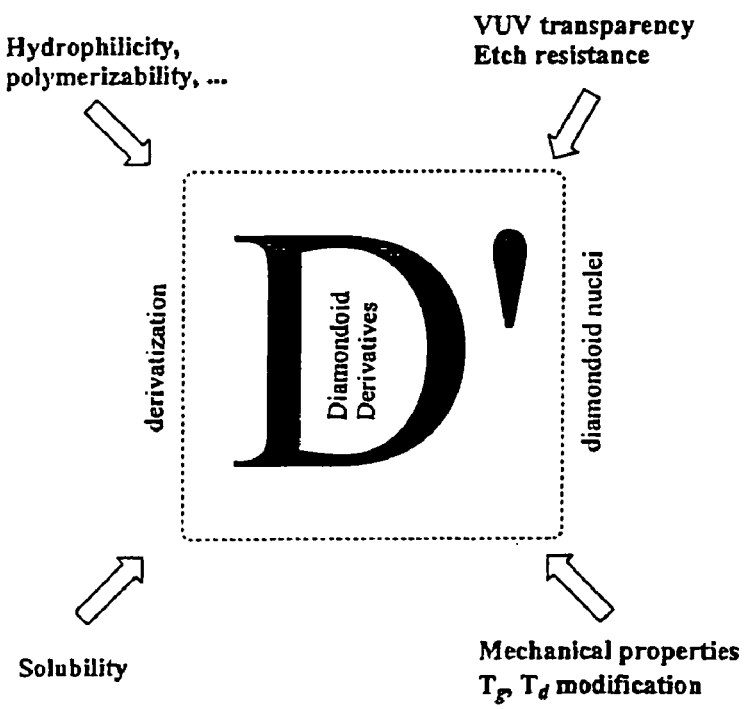
FIG. 5B is a schematic showing how chemistry and processing of diamondoids into derivatized diamondoids contribute to photoresist properties.
Figure 6:
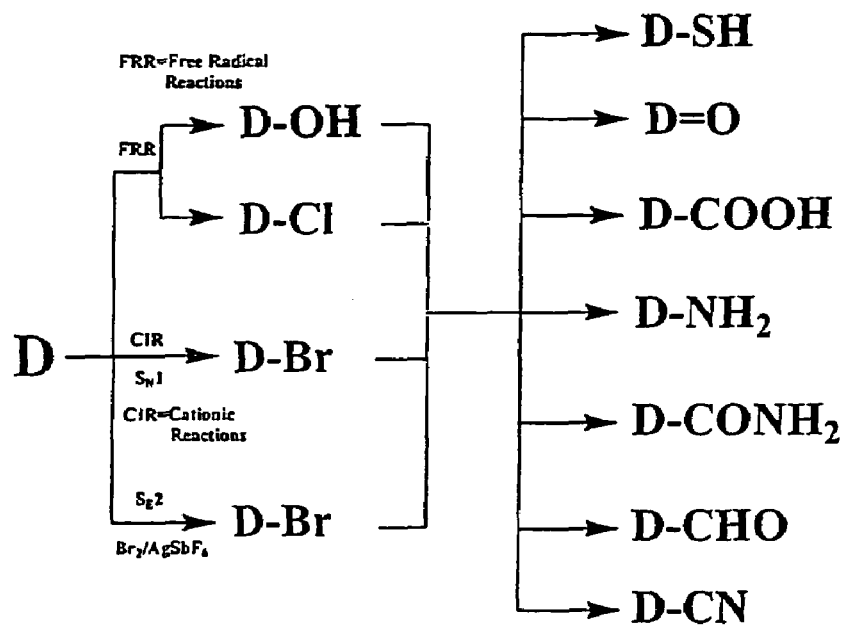
FIGS. 6-20 illustrate exemplary pathways for derivatizing diamondoids.

FIG. 5 shows a flow chart for the strategy of derivatization of diamondoids and FIG. 6 shows some representative primary derivatives of diamondoids and the corresponding reactions. As shown in FIG. 6, there are, in general, three major reactions for the derivatization of diamondoids sorted by mechanism: nucleophilic ($S_N1$-type) and electrophilic ($S_E2$-type) substitution reactions, and free radical reaction (details for such reactions and their use with adamantane are shown, for instance in, "*Recent developments in the adamantane and related polycyclic hydrocarbons*" by R. C. Bingham and P. v. R. Schleryer as a chapter of the book entitled "*Chemistry of Adamantanes*" (Springer-Verlag, Berlin Heidelberg New York, 1971) and in; "*Reactions of adamantanes in electrophilic media*" by I. K. Moiseev, N. V. Makarova, M. N. Zemtsova published in *Russian Chemical Review*, 68(12), 1001-1020 (1999); "*Cage hydrocarbons*" edited by George A. Olah (John Wiley & Son, Inc., New York, 1990).

Figure 7:
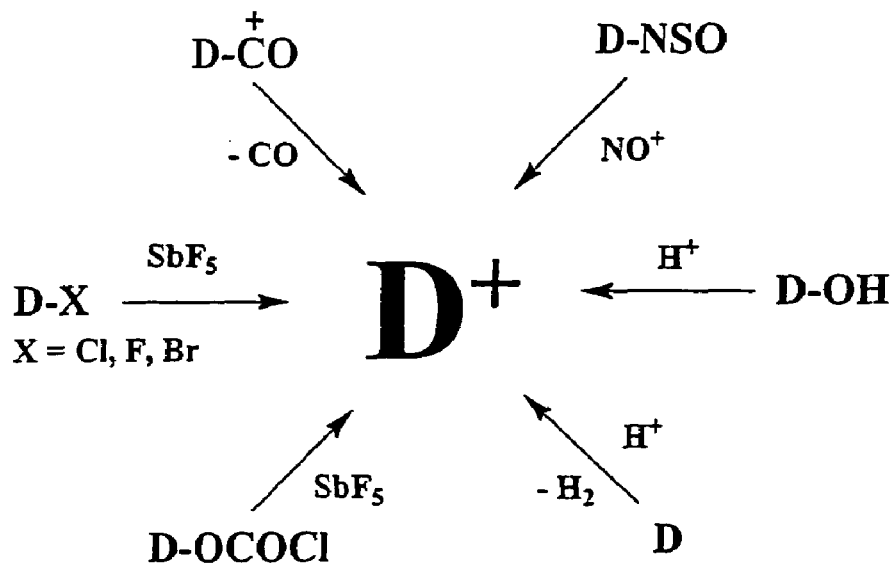
Figure 8:
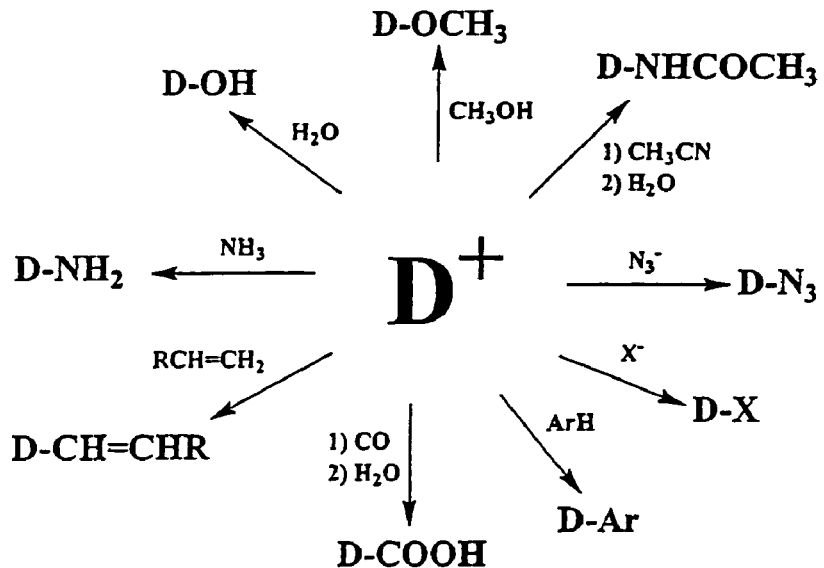
Figure 9:
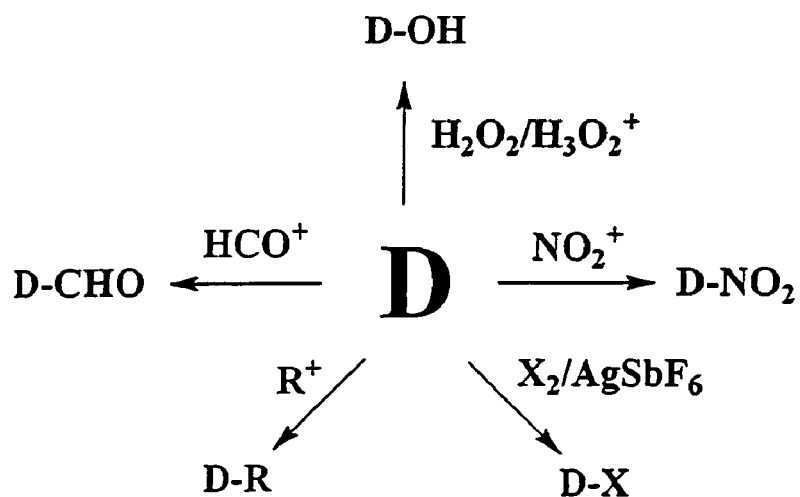

$S_N1$ reactions involve the generation of diamondoid carbocations (there are several different ways to generate the diamondoid carbocations, for instance, the carbocation is generated from a parent diamondoid, a hydroxylated diamondoid or a halogenated diamondoid, shown in FIG. 7), which subsequently react with various nucleophiles. Some representative examples are shown in FIG. 8. Such nucleophiles include, for instance, the following: water (providing hydroxylated diamondoids); halide ions (providing halogenated diamondoids); ammonia (providing aminated diamondoids); azide (providing azidylated diamondoids); nitriles (the Ritter reaction, providing aminated diamondoids after hydrolysis); carbon monoxide (the Koch-Haaf reaction, providing carboxylated diamondoids after hydrolysis); olefins (providing alkenylated diamondoids after deprotonation); and aromatic reagents (providing arylated diamondoids after deprotonation). The reaction occurs similarly to those of open chain alkyl systems, such as t-butyl, t-cumyl and cycloalkyl systems. Since tertiary (bridgehead) carbons of diamondoids are considerably more reactive than secondary carbons under $S_N1$ reaction conditions, substitution at the tertiary carbons is favored. $S_E2$-type reactions (i.e., electrophile substitution of a C—H bond via a five-coordinate carbocation intermediate) include, for instance, the following reactions: hydrogen-deuterium exchange upon treatment with deuterated superacids (e.g., DF—$SbF_5$ or $DSO_3F$—$SbF_5$); nitration upon treatment with nitronium salts, such as $NO_2^+BF_4^-$ or $NO_2^+PF_6^-$ in the presence of superacids (e.g., $CF_3SO_3H$); halogenation upon, for instance, reaction with $Cl_2+AgSbF_6$; alkylation of the bridgehead carbons under the Friedel-Crafts conditions (i.e., $S_E2$-type σ alkylation); carboxylation under the Koch reaction conditions; and, oxygenation under $S_E2$-type σ hydroxylation conditions (e.g., hydrogen peroxide or ozone using superacid catalysis involving $H_3O_2^+$ or $HO_3^+$, respectively). Some representative $SE^2$-type reactions are shown in FIG. 9.

Of those $S_N1$ and $S_E2$ reactions, $S_N1$-type reactions are the most frequently used for the derivatization of diamondoids. However, such reactions produce the derivatives mainly substituted at the tertiary carbons. Substitution at the secondary carbons of diamondoids is not easy in carbonium ion processes since secondary carbons are considerably less reactive than the bridgehead positions (tertiary carbons) in ionic processes. However, reactions at the secondary carbons are achieved by taking advantage of the low selectivity of free radical reactions and the high ratios of 2° (secondary) to 3° (tertiary, bridgehead) hydrogens in diamondoids. Thus, free radical reactions provide a method for the preparation of a greater number of the possible isomers of a given diamondoid than might be available by ionic precesses. The complex product mixtures and/or isomers which result, however, are generally difficult to separate. Due to the decreased symmetry of substituted diamondoids, free radical substitution of these substrates may give rise to very complex product mixtures. Therefore, in most cases, practical and useful free radical substitutions of diamondoids can use photochlorination and/or photooxidation under special circumstances which permit a simpler separation of the product mixture. For instance, photochlorination is particularly useful for the synthesis of chlorinated diamondoids at the secondary carbons and further derivatizations at the secondary carbons because chlorinated diamondoids at the secondary carbons are similar in reactivity to those derivatized at the tertiary carbons.

Photooxidation is another powerful free radical reaction for the synthesis of hydroxylated derivatives at the secondary carbons which are further oxidized to keto derivatives, which can be reduced to alcohols providing unique hydroxylated diamondoid derivatives at the secondary carbons.

Considering this significant advantage of separating the keto diamondoids, a variety of diamondoid derivatives at the secondary carbons are prepared starting from the keto derivatives (diamondoidones), such as by reducing the keto group by, for instance, LiAlH$_4$, to provide the corresponding hydroxylated derivatives at the secondary carbons and further derivatizations at the secondary carbons starting from those hydroxylated derivatives. Diamondoidones can also undergo acid-catalyzed (HCl-catalyzed) condensation reaction with, for example, excess phenol or aniline in the presence of hydrogen chloride to form 2,2-bis(4-hydroxyphenyl) diamondoids or 2,2-bis(4-aminophenyl) higher diamandoids substituted at the secondary carbons. With the development of separation technology, such as by using up-to-date HPLC technique, we may predict that more free radical reactions might be employed for the synthesis of derivatives of diamondoids.

Using those three major types of reactions for the derivatization of diamondoids, a number of diamondoid derivatives are prepared. Representative core reactions and the derivatives are presented as following as either very important means to activate the diamondoid nuclei or very important precursors for further derivatizations.

Figure 10:
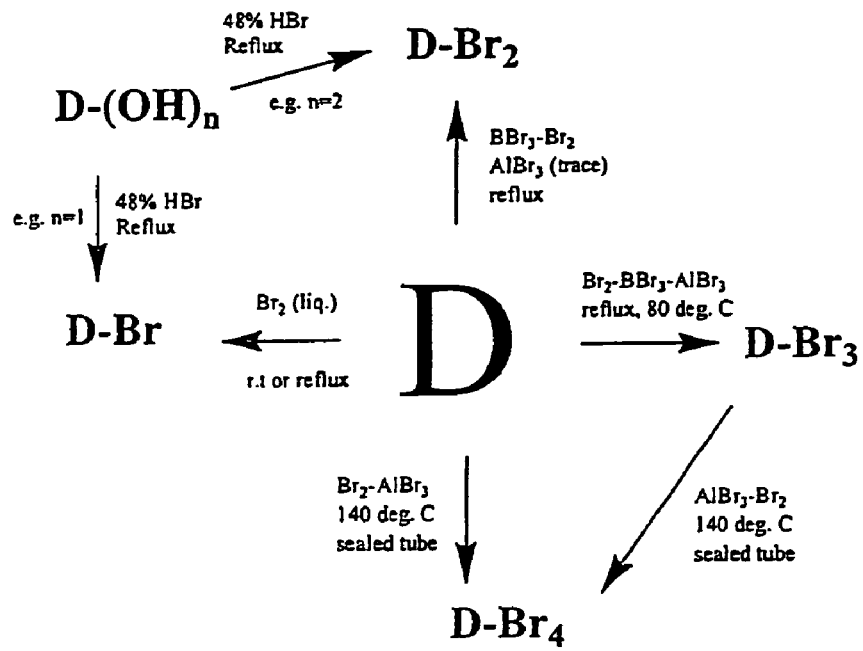

FIG. 10 shows some representative pathways for the preparation of brominated diamondoid derivatives. Mono- and multi-brominated diamondoids are some of the most versatile intermediates in the derivative chemistry of diamondoids. These intermediates are used in, for example, the Koch-Haaf, the Ritter, and the Friedel-Crafts alkylation/arylation reactions. Brominated diamondoids are prepared by two different general routes. One involves direct bromination of diamondoids with elemental bromine in the presence or absence of a Lewis acid (e.g. BBr$_3$—AlBr$_3$) catalyst. The other involves the substitution reaction of hydroxylated diamondoids with hydrobromic acid.

Direct bromination of diamondoids is highly selective resulting in substitution at the bridgehead (tertiary) carbons. By proper choice of catalyst and conditions, one, two, three, four, or more bromines can be introduced sequentially into the molecule, all at bridgehead positions. Without a catalyst, the mono-bromo derivative is the major product with minor amounts of higher bromination products being formed. By use of suitable catalysts, however, di-, tri-, and tetra-, penta-, and higher bromide derivatives of diamondoids are isolated as major products in the bromination (e.g., adding catalyst mixture of boron bromide and aluminum bromide with different molar ratios into the bromine reaction mixture). Typically, tetrabromo or higher bromo derivatives are synthesized at higher temperatures in a sealed tube.

To prepare bromo derivatives substituted at secondary carbons, for example, the corresponding hydroxylated diamondoids at the secondary carbons is treated under mild conditions with hydrobromic acid. Preferably, diamondoids hydroxylated at secondary carbons are prepared by the reduction of the corresponding keto derivative as described above.

Bromination reactions of diamondoids are usually worked up by pouring the reaction mixture onto ice or ice water and adding a suitable amount of chloroform or ethyl ether or carbon tetrachloride to the ice mixture. Excess bromine is removed by distillation under vacuum and addition of solid sodium disulfide or sodium hydrogen sulfide. The organic layer is separated and the aqueous layer is extracted by chloroform or ethyl ether or carbon tetrachloride for an additional 2-3 times. The organic layers are then combined and washed with aqueous sodium hydrogen carbonate and water, and finally dried.

To isolate the brominated derivatives, the solvent is removed under vacuum. Typically, the reaction mixture is purified by subjecting it to column chromatography on either alumina or silica gel using standard elution conditions (e.g., eluting with light petroleum ether, n-hexane, or cyclohexane or their mixtures with ethyl ether). Separation by preparative gas chromatography (GC) or high performance liquid chromatography (HPLC) is used where normal column chromatography is difficult and/or the reaction is performed on extremely small quantities of material.

Figure 11:
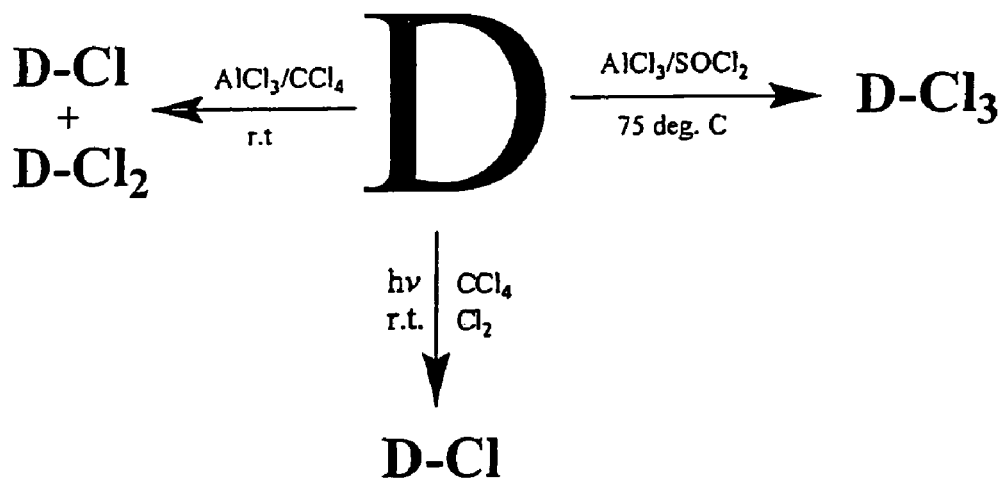

Similarly to bromination reactions, diamondoids are chlorinated or photochlorinated to provide a variety of mono-, di-, tri-, or even higher chlorinated derivatives of the diamondoids. FIG. 11 shows some representative pathways for the synthesis of chlorinated diamondoid derivatives, especially those chlorinated derivatives at the secondary carbons by way of photochlorination.

Figure 12:
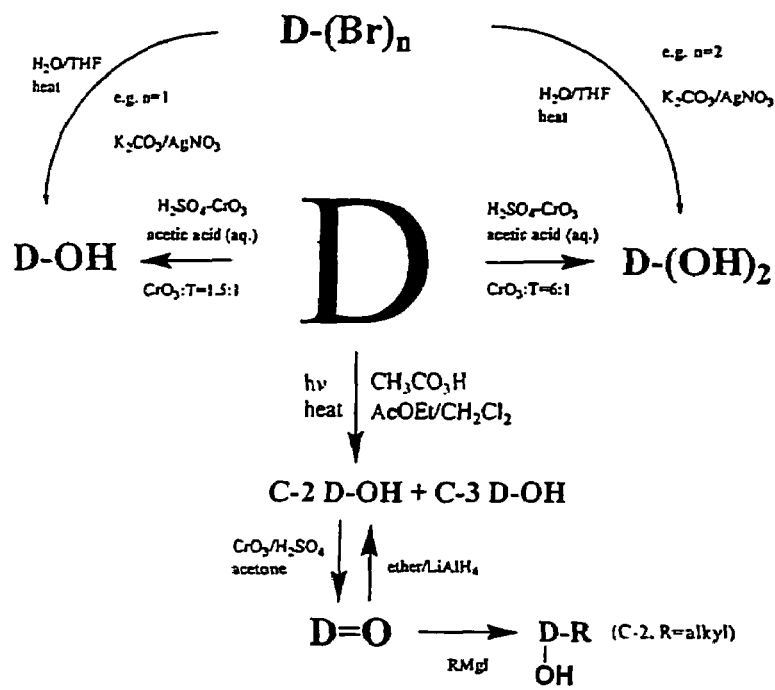

FIG. 12 shows some representative pathways for the synthesis of hydroxylated diamondoids. Direct hydroxylation is also effected on diamondoids upon treatment with N-hydroxyphthalimide and a binary co-catalyst in acetic acid. Hydroxylation is a very important way of activating the diamondoid nuclei for further derivatizations, such as the generation of diamondoid carbocations under acidic conditions, which undergo the $S_N1$ reaction to provide a variety of diamondoid derivatives. In addition, hydroxylated derivatives are very important nucleophilic agents, by which a variety of diamondoid derivatives are produced. For instance, the hydroxylated derivatives are esterified under standard conditions such as reaction with an activated acid derivative. Alkylation to prepare ethers is performed on the hydroxylated derivatives through nucleophilic substitution on appropriate alkyl halides.

The above described three core derivatives (hydroxylated diamondoids and halogenated especially brominated and chlorinated diamondoids), in addition to the parent diamondoids or substituted diamondoids directly separated from the feedstocks as described above, are most frequently used for further derivatizations of diamondoids, such as hydroxylated and halogenated derivatives at the tertiary carbons are very important precursors for the generation of higher diamondiod carbocations, which undergo the $S_N1$ reaction to provide a variety of diamondoid derivatives thanks to the tertiary nature of the bromide or chloride or alcohol and the absence of skeletal rearrangements in the subsequent reactions. Examples are given below.

Figure 13:
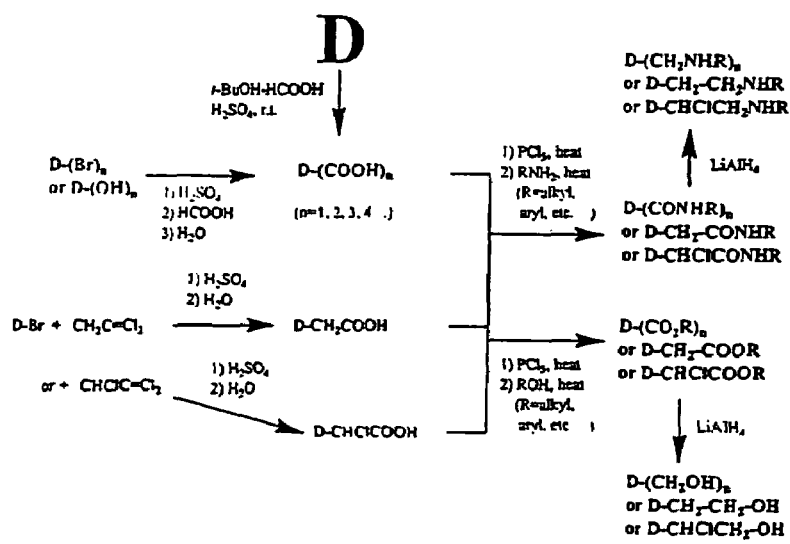

FIG. 13 shows some representative pathways for the synthesis of carboxylated diamondoids, such as the Koch-Haaf reaction, starting from hydroxylated or brominated diamondoids. It should be mentioned that for most cases, using hydroxylated precursors get better yields than using brominated diamondoids. For instance, carboxylated derivatives are obtained from the reaction of hydroxylated derivatives with formic acid after hydrolysis. The carboxylated derivatives are further esterified through activation (e.g., conversion to acid chloride) and subsequent exposure to an appropriate alcohol. Those esters are reduced to provide the corresponding hydroxymethyl diamondoids (diamondoid substituted methyl alcohols, D-CH$_2$OH). Amide formation is also performed through activation of the carboxylated derivative and reaction with a suitable amine. Reduction of the diamondoid carboxamide with reducing agents (e.g.

lithium aluminum hydride) provides the corresponding aminomethyl diamondoids (diamondoid substituted methylamines, D-CH$_2$NH$_2$).

Figure 14:
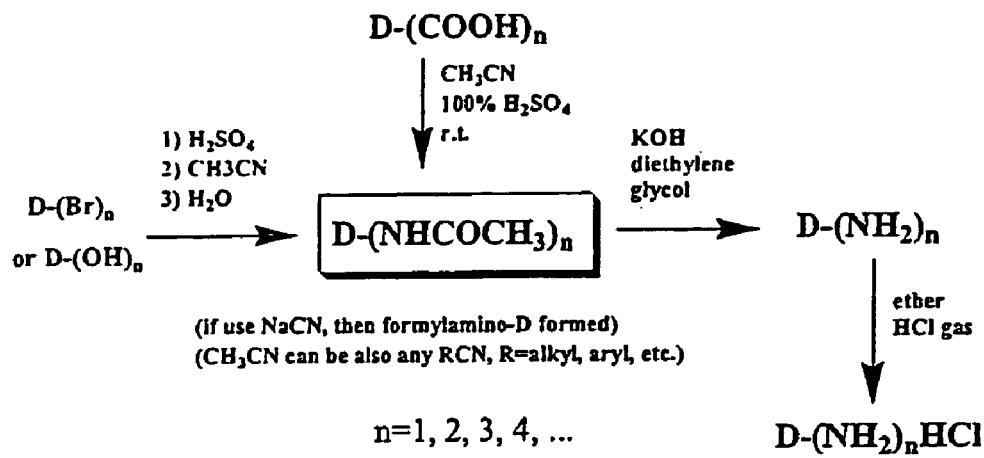
Figure 15:
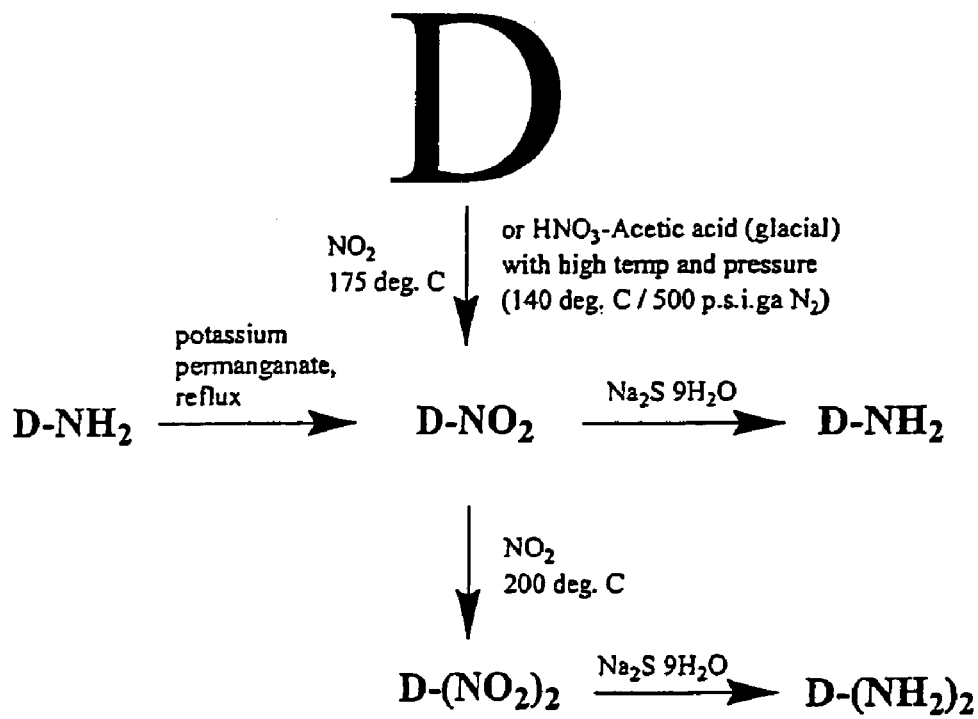

FIG. 14 shows some representative pathways for the synthesis of acylaminated diamondoids, such as the Ritter reaction starting from hydroxylated or brominated diamondoids. Similarly to the Koch-Haaf reaction, using hydroxylated precursors get better yields than using brominated diamondoids in most cases. Acylaminated diamondoids are converted to amino derivatives after alkaline hydrolysis. Amino diamondoids are further converted to, without purification in most cases, amino diamondoid hydrochloride by introducing hydrochloride gas into the aminated derivatives solution. Amino diamondoids are some of very important precursors in the synthesis of medicines. They are also prepared from the reduction of nitrated compounds. FIG. 15 shows some representative pathways for the synthesis of nitro diamondoid derivatives. Diamondoids are nitrated by concentrated nitric acid in the presence of glacial acetic acid under high temperature and pressure. The nitrated diamondoids are reduced to provide the corresponding amino derivatives. In turn, for some cases, amino diamondoids are oxidized to the corresponding nitro derivatives if necessary. The amino derivatives are also synthesized from the brominated derivatives by heating them in the presence of formamide and subsequently hydrolyzing the resultant amide.

Similarly to the hydroxylated compounds, amino higher diamonds are acylated or alkylated. For instance, reaction of an amino diamondoid with an activated acid derivative produces the corresponding amide. Alkylation is typically performed by reacting the amine with a suitable carbonyl containing compound in the presence of a reducing agent (e.g. lithium aluminum hydride). The amino diamondoids undergo condensation reactions with carbamates such as appropriately substituted ethyl N-arylsulfonylcarbamates in hot toluene to provide, for instance, N-arylsulfonyl-N'-diamondoidylureas.

Figure 16:
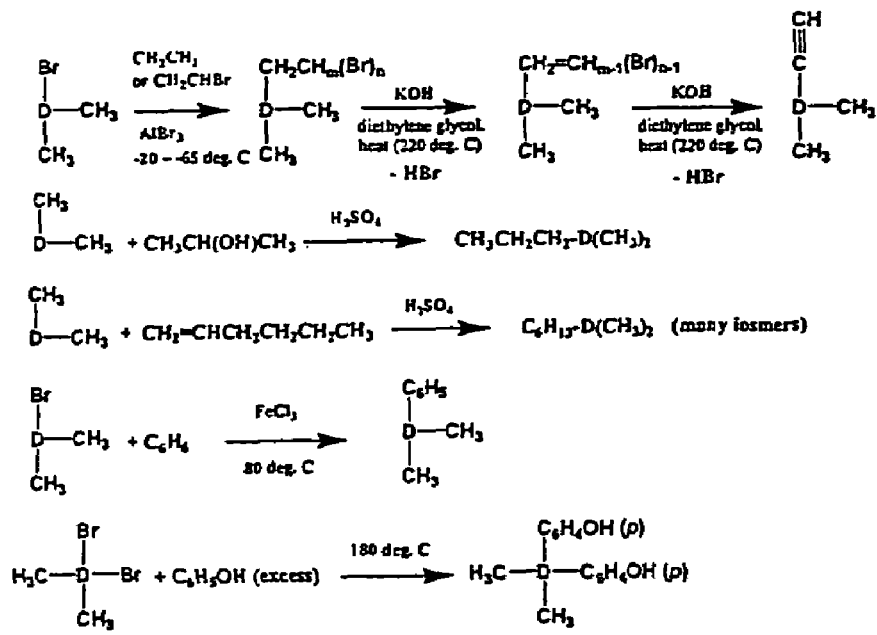

FIG. 16 presents some representative pathways for the synthesis of alkylated, alkenylated, alkynylated and arylated diamondoids, such as the Friedel-Crafts reaction. Ethenylated diamondoid derivatives are synthesized by reacting a brominated diamondoid with ethylene in the presence of AlBr$_3$ followed by dehydrogen bromide with potassium hydroxide (or the like). The ethenylated compound is transformed into the corresponding epoxide under standard reaction conditions (e.g., 3-chloroperbenzoic acid). Oxidative cleavage (e.g., ozonolysis) of the ethenylated diamondoid affords the related aldehyde. The ethynylated diamondoid derivatives are obtained by treating a brominated diamondoid with vinyl bromide in the presence of AlBr$_3$. The resultant product is dehydrogen bromide using KOH or potassium t-butoxide to provide the desired compound.

More reactions are illustrative of methods which can be used to functionalize diamondoids. For instance, fluorination of a diamondoid is carried out by reacting the diamondoid with a mixture of poly(hydrogen fluoride) and pyridine (30% Py, 70% HF) in the presence of nitronium tetrafluoroborate. Sulfur tetrafluoride reacts with a diamondoid in the presence of sulfur monochloride to afford a mixture of mono-, di-, tri- and even higher fluorinated diamondoids. Iodo diamondoids are obtained by a substitutive iodination of chloro, bromo or hydroxyl diamondoids.

Reaction of the brominated derivatives with hydrochloric acid in dimethylformamide (DMF) converts the compounds to the corresponding hydroxylated derivatives. Brominated or iodinated diamondoids are converted to thiolated diamondoids by way of, for instance, reacting with thioacetic acid to form diamondoid thioacetates followed by removal of the acetate group under basic conditions. Brominated diamondoids, e.g. D-Br, is heated under reflux with an excess (10 fold) of hydroxyalkylamine, e.g. HO—CH$_2$CH$_2$—NH$_2$, in the presence of a base, e.g. triethylamine, diamondoidyloxyalkylamine, e.g. D-O—CH$_2$CH$_2$—NH$_2$, is obtained. On acetylation of the amines with acetic anhydride and pyridine, a variety of N-acetyl derivatives are obtained. Direct substitution reaction of brominated diamondoids, e.g. D-Br, with sodium azide in dipolar aprotic solvents, e.g. DMF, to afford the azido diamondoids, e.g. D-N$_3$.

Figure 17:
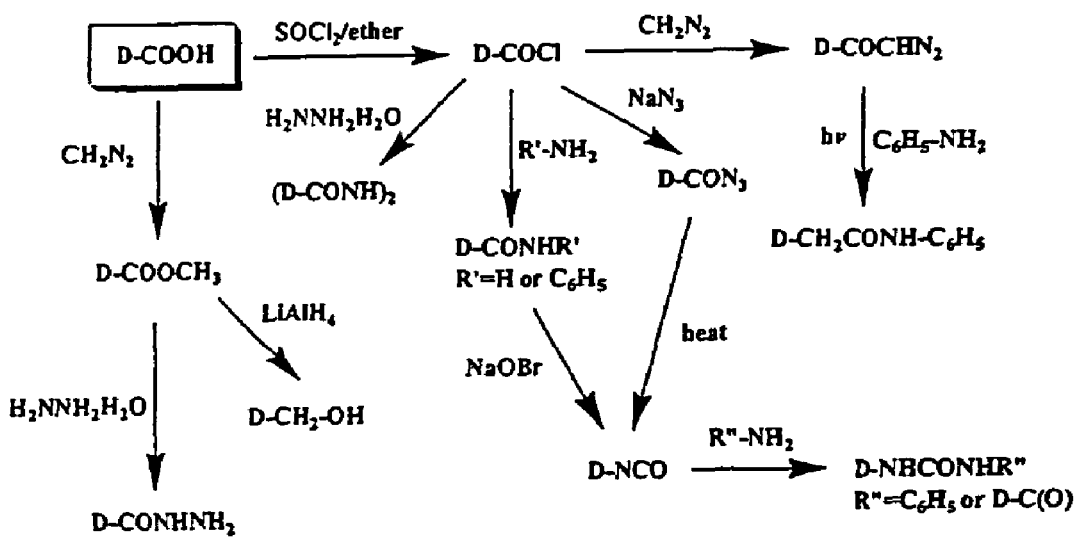

Diamondoid carboxylic acid hydrazides are prepared by conversion of diamondoid carboxylic acid into a chloroanhydride by thionyl chloride and condensation with isonicotinic or nicotinic acid hydrazide (FIG. 17).

Diamondoidones or "diamondoid oxides" are synthesized by photooxidation of diamondoids in the presence of peracetic acid followed by treatment with a mixture of chromic acid-sulfuric acid. Diamondoidones are reduced by, for instance, LiAlH$_4$, to diamondoidols hydroxylated at the secondary carbons. Diamondoidones also undergo acid-catalyzed (HCl-catalyzed) condensation reaction with, for example, excess phenol or aniline in the presence of hydrogen chloride to form 2,2-bis(4-hydroxyphenyl) diamondoids or 2,2-bis(4-aminophenyl) diamondoids.

Diamondoidones (e.g. D=O) are treated with RCN (R=hydrogen, alkyl, aryl, etc.) and reduced with LiAlH$_4$ to give the corresponding C-2-aminomethyl-C-2-D-OH, which are heated with COCl$_2$ or CSCl$_2$ in toluene to afford the following derivatives shown in formula IV (where Z=O or S):

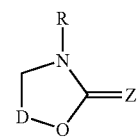

IV

Diamondoidones react with a suitable primary amine in an appropriate solvent to form the corresponding imines. Hydrogenation of the imines in ethanol using Pd/C as the catalyst at about 50° C. to afford the corresponding secondary amines. Methylation of the secondary amines following general procedures (see, for instance, H. W. Geluk and V. G. Keiser, *Organic Synthesis*, 53:8 (1973)) to give the corresponding tertiary amines. Quaternization of the tertiary amines by, for instance, slowly dropping CH$_3$I (excess) into an ethanol solution of the amine at around 35° C. to form the corresponding quaternary amines.

C-2 derivatives of diamondoids, C-2 D-R' (R'=alkyl, alkoxy, halo, OH, Ph, COOH, CH$_2$COOH, NHCOCH$_3$, CF$_3$COOH) are prepared by nucleophilic substitution of diamondoid-C-2-spiro-C-3-diazirine in solution at 0-80° C. in the presence of an acid catalyst.

N-sulfinyl diamondoids [D-(NSO)$_n$, n=1, 2, 3, 4, . . . ] are prepared by refluxing the diamondoid-HCl with SOCl$_2$ in benzene for about half an hour to several hours afording mono-, di, tri-, or higher N-sulfinyl diamondoid derivatives.

Treatment of D-Br and/or D-Cl with HCONH$_2$ (wt. ratio not >1:2) at <195° C. followed by hydrolysis of the formylamino diamondoids D-NHCHO with <20% HCl at <110° C. affords the amino diamondoid hydrochloride D-NH$_2$HCl.

Diamondoid dicarboxamides are prepared by the reaction of diamondoid dicarbonyl chloride or diamondoid diacetyl chloride with aminoalkylamines. For instance, D-(COCl)$_2$ [from SOCl$_2$ and the corresponding dicarboxylic acid D-(COOH)$_2$] are treated with (CH$_3$)$_2$NCH$_2$CH$_2$CH$_2$NH$_2$ in C$_5$H$_5$N—C$_6$H$_6$ to give N,N'-bis(dimethylaminopropyl) diamondoid dicarboxamide.

Aminoethoxyacetylamino diamondoids are prepared from chloroacetylamino diamondoids and HOCH$_2$CH$_2$NR'R". Thus, for instance, amino diamondoids, D-NH$_2$, and ClCH$_2$COCl in benzene, is added to (CH$_3$)$_2$NCH$_2$CH$_2$ONa in xylene and refluxed for about 10 hours to give aminoethoxyacetylamino diamondoids (R'=R"=CH$_3$).

Ritter reaction of C-3 D-OH and HCN gives D-NH$_2$; the preparation of D-NHCHO from diamondoids and HCN; the reaction of diamondoids with nitriles gives D-NHCHO and D-NH$_2$; the preparation of aza diamondoids from nitriles and compounds containing unsaturated OH groups, and SH groups, and so on.

Hydroxylated diamondoids, e.g. D-OH, react with COCl$_2$ or CSCl$_2$ to afford the diamondoidyloxycarbonyl derivatives, e.g. D-O—C(O)Cl or D-O—C(S)Cl the former being an important blocking group in biochemical syntheses.

Figure 18:
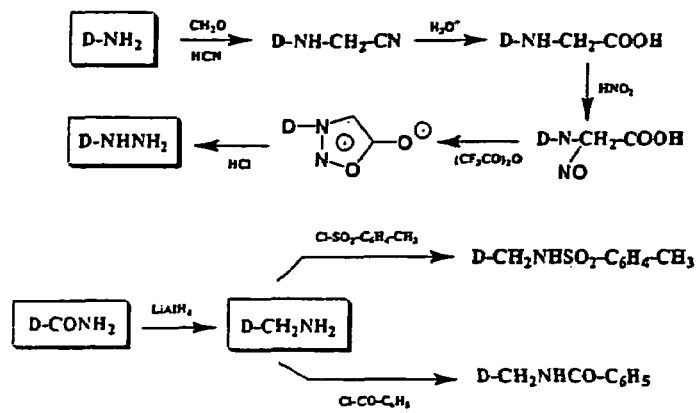

FIG. 18 shows representative reactions starting from D-NH$_2$ and D-CONH$_2$ and the corresponding derivatives, wherein D is a diamondoid nucleus.

Figure 19:
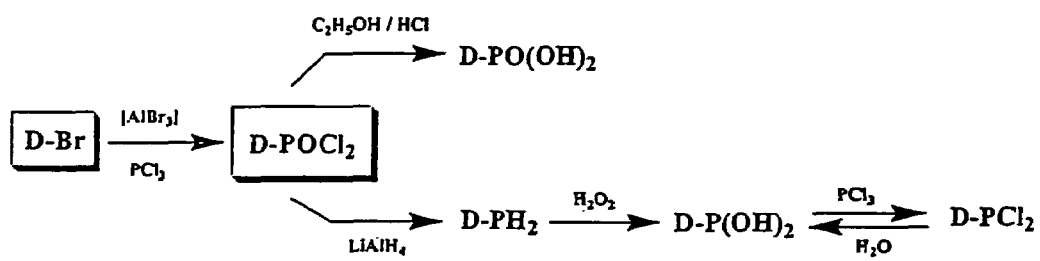

FIG. 19 shows representative reactions starting from D-POCl$_2$ and the corresponding derivatives, wherein D is a diamondoid nucleus.

Figure 20:
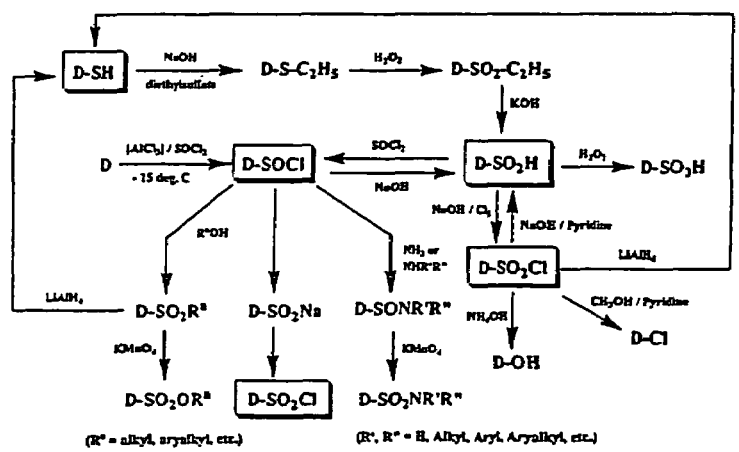

FIG. 20 shows representative reactions starting from D-SH or D-SOCl and the corresponding derivatives, wherein D is a diamondoid nucleus.

Polymerizable Diamantyl, and Triamantyl and Higher Diamondoid Containing Monomers Embodiments of the present invention specifically include polymerizable diamantyl monomers having the formula Pg-D-(R)$_n$, wherein D is a diamantyl nucleus; Pg is a polymerizable group covalently bonded to a carbon of the diamantyl nucleus; n is an integer ranging from 1 to 6, inclusive; at least one of the R's is a hydrophilic-enhancing moiety; and each of the remaining R's is independently selected from the group consisting of hydrogen and a hydrophilic-enhancing moiety. The hydrophilic-enhancing moietyies of these diamantyl monomers may be selected from the group consisting of a hydroxyl group —OH, a carboxylic group —COOH, an alkyl group —OCH$_3$ or —OC$_2$H$_5$, a keto group —C(O)—, and a group —OC(O)—OCH$_3$ or —OC(O)—OC$_2$H$_5$.

Other embodiments of the present invention provide for triamantyl monomers having polymerizable groups and hydrophilic-enhancing moities similar to those for diamantyl monomers discussed above, as well as diamonoid-containing monomers with polymerizable groups and hydrophilic-enhancing moities, wherein the diamondoid portion of the diamonoid-containing monomer is selected from the group consisting of tetramantane, pentamantane, hexamantane, heptamantane, octamantane, nonamantane, decamantane, and undecamantane.

In other embodiments of the present invention, the polymerizable groups Pg of the diamantyl, triamantyl, higher diamondoid containing monomers are capable of forming photo-labile polymers. The polymerizable groups may be covalently bonded to either secondary (2°) carbons or tertiary carbons (3°, also called bridgehead carbons) of the diamantyl, triamantyl, or higher diamondoid nucleus. These polymerizable groups may comprise an unsaturated acid residue bound to the diamantyl, triamantyl, or higher diamondoid nucleus to form an ester, and the unsaturated acid residue may comprise an acrylate or a lower alkyl acrylate. When the unsaturated acid residue is an acrylic acid residue the respective monomer becomes an acrylate monomer. Similarly, when the unsaturated acid residue is an methacrylic acid residue the respective monomer becomes an methacrylate monomer.

Further embodiments of the present invention provide for methods of forming a layer of patterned photoresist on the surface of a substrate. Such methods comprise the steps of:

a) forming a polymer from monomers selected from the group consisting of a diamantyl monomer having a polymerizable group and at least one hydrophilic-enhancing group; a triamantyl monomer having a polymerizable group and at least one hydrophilic-enhancing group; and a diamondoid-containing monomer having a polymerizable group and at least one hydrophilic-enhancing group, the diamondoid of the diamondoid-containing monomer selected from the group consisting of tetramantane, pentamantane, hexamantane, heptamantane, octamantane, nonamantane, decamantane, and undecamantane;

b) depositing the polymer on a surface of the substrate as a polymeric layer, the polymeric layer comprising a photo-labile polymer; and c) exposing selected regions of the polymerized layer to an electromagnetic beam, thereby modifying the photo-labile polymer in those regions exposed to the electromagnetic beam to yield a selectively modified layer.

According to further embodiments, the method described above may include the step of contacting the selectively modified layer with a solvent system to solubilize the modified regions. The electromagnetic beam may comprise radiation having a wavelength less than about 200 nm, and exemplary wavelenths are 193 nm and 157 nm. The electromagnetic beam may also be an e-beam or an x-ray beam.

As will be explained, one excellent application for these monomers and polymers is as components of photoresists. In this application the monomers and polymers can serve as components of deposited layers. These layers are additional aspects of this invention as are patterned layers and methods of preparing them all of which employ the instant diamantyl and/or triamantyl monomers and polymers.

Photoresist Base Resins

Prior art polymers that have been used in positive-acting photoresists have been discussed by K. Nozaki and E. Yano in "High-Performance Resist Materials for ArF Eximer Laser and Electron Beam Lithography," Fujitsu Sci. Tech. J., 38, 1, p. 3-12 (June, 2002). These authors teach that conventionally, polyvinylphenol-based resists were generally used in electron beam lithography, and such resins made use of a variety of protecting groups such as acetals, tert-butoxycarbonyl, and tert-butyl. The disadvantages of these protecting groups included a poor dry-etch resistance due to the aliphatic structures. To overcome this problem, K. Nozaki and E. Yano suggested the use of acid sensitive and dry etch resistant protective groups. These authors teach that dry etch resistance may be imparted to the resist by incorporating acid cleavable alicyclic substituents into the base polymer.

K. Nozaki and E. Yano reported on the use of mevalonic lactone methacrylate (MLMA) and 2-methyl-2-adamantane methacrylate (MAdMA) based copolymers. The adamantyl, polycyclic hydrocarbon substituent provided superior sensitivity, resolution, and dry etch resistance, whereas the lactone containing monomer afforded compatibility with conventional developers such as tetramethylammonium hydroxide (TMAH), and adhesion to silicon substrates. The adamantane and lactone substituents were chosen since they can function as acid labile ester groups in the methacrylate polymer. The hydrophilic mevalonic lactone group provided adhesion to the silicon substrate, and was acid cleavable because it contained an acid sensitive β-hydroxyketone structure and a tertiary alcohol. The alicyclic adamantyl substituent provided dry etch resistance, and was also acid cleavable because of a tertiary alcohol. These authors teach that the adamantyl groups have a stronger dissolution inhibition than, for example, a t-butyl pendant group would have, which comes about from its highly hydrophobic nature and bulky structure. Thus, a large polarity change can be obtained with a small amount of deprotection, and therefore a superior contrast between exposed and unexposed regions of the resist may be realized, contributing to enhance resolution.

Of particular interest is the imaging results obtained by K. Nozaki and E. Yano. A series of five methacrylate polymers were prepared, wherein the ratios of the monomers MLMA/MAdMA ranged from 0/100, 22/78, 51/49, 72/28, and 100/0, respectively. The polymers prepared from the latter two monomer ratios could not be imaged because they were alkali soluble, and it was not possible to resolve any resist patterns. Furthermore, the polymer prepared from the 100/0 ratio was difficult to spin-coat because the photo-acid generator separated out from the resist composition. The polymers prepared from the first two monomer ratios likewise did not image well (or could not be imaged) because the formulated resist patterns peeled off the silicon substrates, suggesting that the rigid adamantyl units imparted a brittleness to the resist. The photoresist composition containing roughly equal amounts of the two monomers was thought to be a promising compromise, and based on their observations, the optimum composition for the base polymer was about MAdMA/MLMA=1/1.

The photoresist compositions of the present embodiments include acid-cleavable diamondoid blocking groups higher in the homologous series than adamantane. The advantages of including such diamondoids is that an enhanced etch resistance may be imparted to the base resin, thereby improving the resolution of the resist, but the choice of diamondoid higher than adamantane, the amounts in which it is used, and the number of hydrophilic-enhancing groups with which it is derivatized, comprise a part of the subject matter of the present disclosure.

Co-Polymer Base Resins with Diamondoids Higher than Adamantane

Figure 21:
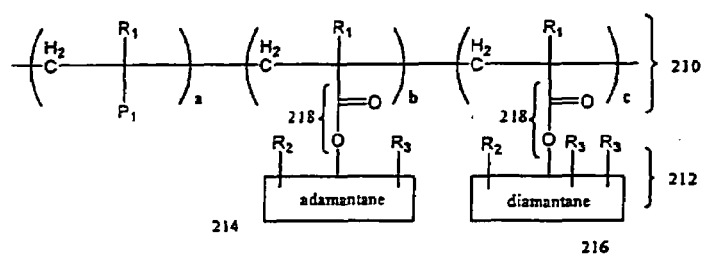
FIGS. 21A-B illustrate exemplary base resins of the present invention, wherein the base resin contains a diamondoid pendant group higher in the polymantane series than adamantane (although they may contain adamantane as well)
FIGS. 21C-D illustrate exemplary non-diamondoid, lactone containing pendant groups.
Figure 21:
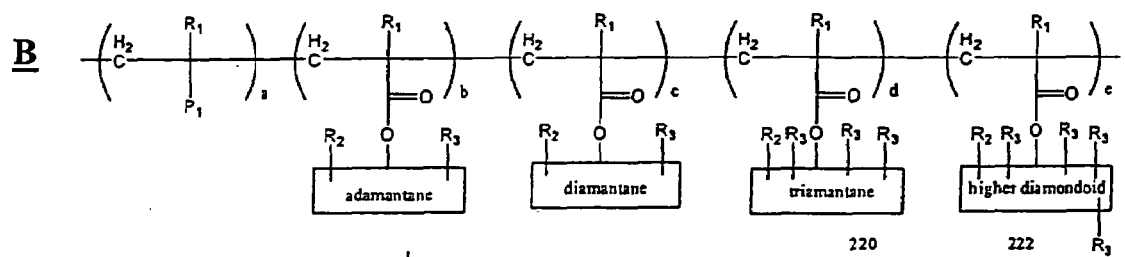
Figure 21:
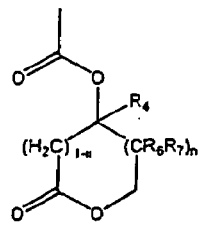
Figure 21:
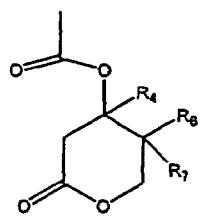

According to embodiments of the present invention, the base resin of a positive-acting photoresist may be represented by the general formula illustrated in FIGS. 21A-C. The positive-working photoresist composition shown in FIG. 21A comprises a polymeric backbone chain 210, which may include pendant groups 212. The pendant groups 212 may be a non-diamondoid pendant group represented by $P_1$, or the pendant groups may be diamondoid-containing such as the adamantane based pendant group 214 or the diamantane based pendant group 216. In this example, the pendant groups 212 are connected to the main backbone chain 210 through ester groups 218, which is the linkage that imparts the acid-cleavable character to the base resin shown in FIG. 21A. Also depicted in FIG. 21 A are alkyl groups $R_2$ that yield a tertiary alcohol when the blocking groups 214 and 216 are cleaved, as well as hydrophilic-enhancing groups $R_3$.

Specifically, in this exemplary base resin, $R_1$ may be either —H or —$CH_3$, such that the polymeric backbone chain 210 constitutes either an acrylate type polymer, or a methacrylate type polymer, respectively. $R_2$ in this example may be either —H, in which case the diamondoid-containing monomer is not acid cleavable, or an alkyl (such as —$CH_3$) group having from 1 to 4 carbon atoms. In the latter case the diamondoid-containing pendant group is acid cleavable because the capability of forming a carbon-carbon double bond exists. The dissolution ability of the pendant group (i.e., the ability of the pendant group to dissolve in an alkali developer) is enhanced by the fact that a tertiary alcohol is formed when $R_2$ is an alkyl group or an alkoxy group. $R_3$ is either —H, or a hydrophilic-enhancing moiety that may be either a hydroxyl group —OH, a carboxylic gropup —COOH, an alkyl group —$OR_4$, a keto group —C(O)—, or —OC(O)—$OR_4$. It will be apparent to those skilled in the art that —$OR_4$ represents the situation when an alcohol group —OH is protected, wherein the protection may be in the form of an alkyl group or an acetate group.

One feature of the present embodiments that contribute to their novelty is the fact that, unlike the base polymers taught by K. Nozaki and E. Yano, a monomer having a diamondoid pendant group higher than adamantane is included in the base resin. This exemplary monomer that contains a pendant group higher than adamantane is shown in FIG. 21A as diamantane. The advantages of including monomers with diamondoid-containing pendant groups higher than adamantane is that since because there are more carbons present in the $sp^3$-hybridized, diamond cubic crystal structure, the blocking group is more resistant to the etching process, and thus, the exposed and unexposed regions of the resist are more delineated. This feature enhances resolution. Furthermore, because the etch resistance has been improved, it may be possible to incorporate less of the diamantane containing monomer into the base resin, improving the ability of the resist to adhere to the substrate.

According to embodiments of the present invention, the ratios of the feed monomers for the exemplary base resin depicted in FIG. 21A may be represented by the relationships:

a is 0.25 to 0.75;

$b+c=1-a$; and c is greater than zero, where a, b, and c represent the relative amounts of the non-diamondoid containing monomer, the adamantane-containing monomer, and the diamantane-containing monomer, respectively. It will be understood by those skilled in the art that the formula shown in FIG. 21A is schematic only, and that the repeat units represented in quantities a, b, and c may appear in virtually any order in the polymer chain. In other words, the repeat units do not have to follow the pattern a, b, c, a, b, c, and may instead take the form a, a, b, a, c, a, b, b, a, b, c, a, c, b, etc.

A consequence of including monomers with diamondoid-containing pendant groups higher than adamantane is that the pendant group will be more hydrophobic, and thus it will be more difficult to dissolve the blocking group in the alkali developer. This issue may be addressed, however, by derivatizing the diamantane or higher pendant group with a larger number of hydrophilic-enhancing groups, such as the —OH group $R_3$. The number of these that are required is also the subject matter of the present disclosure.

The diamondoid-containing monomer having a pendant group higher than adamantane is not limited to diamantane, and may in fact comprise triamantane 220, and diamondoids 222 that are even higher than triamantane in the polymantane hydrocarbon series. This is illustrated in FIG. 21B. The term "diamondoid" in FIG. 21B is meant to represent any of the diamondoids tetramantane, pentamantane, hexamantane, heptamantane, octamantane, nonamantane, decamantane, and undecamantane. Again, the order of the repeat units in the chain is not limited to that shown in FIG. 21B, as this is just a schematic drawing of an exemplary polymer. If the polymer contains either or both diamantane and triamantane, and even diamondoids, the amounts of these repeat units (which may be the same thing as saying the relative amounts of the monomers in the feed, depending on the reactivity of the monomers during the polymerization process), may be represented by c, d, and e, respectively.

In the exemplary polymer of FIG. 21A, $P_1$ is a non-diamondoid, acid-cleavable pendant group that may be represented by the structures shown in FIGS. 21C-D. The value of "n" may be either 0 or 1. If n=0, then the non-diamondoid pendant group shown in FIG. 21C comprises a five-membered heterocyclic ring with no $R_6$ or $R_7$ substituents on the ring. If n=1, then the non-diamondoid pendant group shown in FIG. 21C comprises a five-membered heterocyclic ring with substituents $R_6$ or $R_7$ on the alpha carbon relative to where the ring attaches to the main polymeric backbone. Again, the linkage in this exemplary polymer is an ester linkage, making the polymer an acrylate or methacrylate, but many other types of linkages are possible.

A six-membered heterocyclic ring for the non-diamondoid, acid-cleavable pendant group $P_1$ is shown in FIG. 21D. In this case, again exemplary, the substituents $R_6$ or $R_7$ are always present on the alpha carbon.

Figure 22:
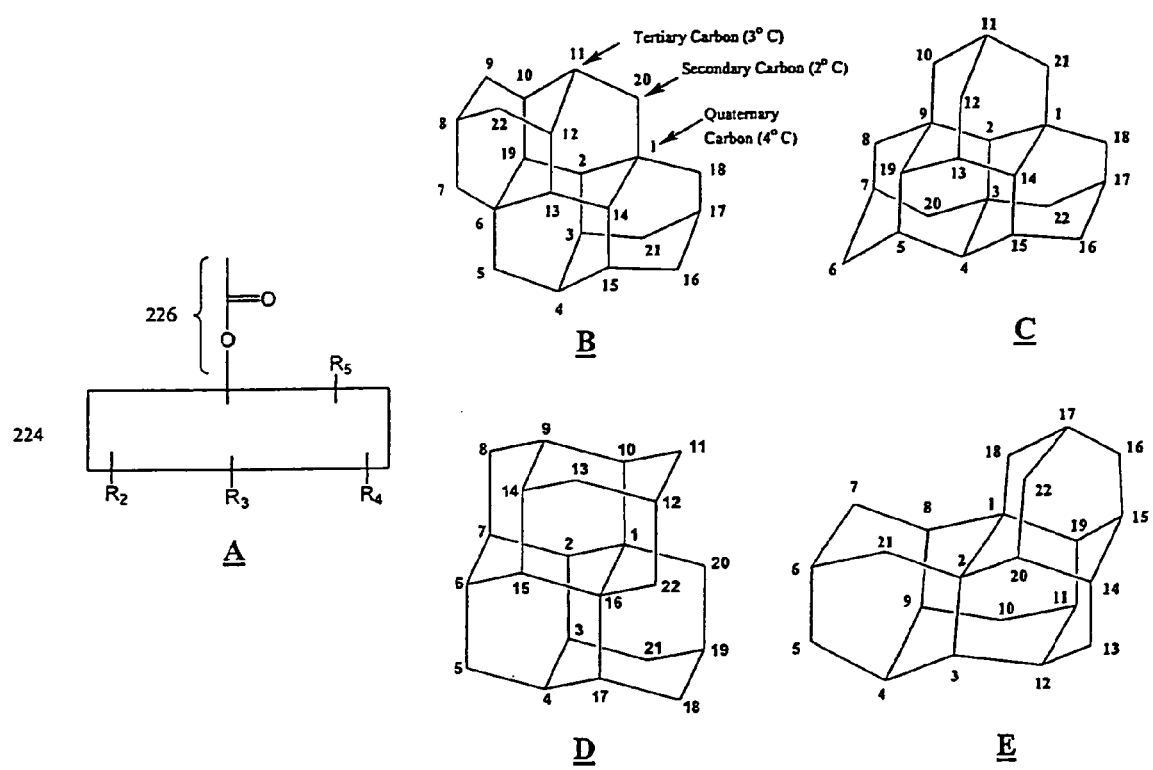
FIGS. 22A-E gives nomenclature for the present structural formulas, illustrating how the hydrophilic-enhancing and polymerizable substituents on the diamondoids higher than adamantane have a variety of attachment points.

It will be understood by those skilled in the art that the nomenclature used in FIGS. 21A-B is meant to represent that there are multiple attachment sites for the exemplary substituent groups $R_2$ and $R_3$ onto the carbon framework of the pendant diamondoid group. An example of this concept is illustrated schematically in FIGS. 22A-E. An exemplary diamondoid pendant group tetramantane is shown at 224 in FIG. 22A. The tetramantane pendant group 224 is attached to the main polymer chain by ester linkage 226, as before. The tetramantane molecule is shown as containing substituents $R_2$, $R_3$, $R_4$, and $R_5$, and the nomenclature in FIG. 22A is meant to indicate that these substituents may be attached at a number of possible sites to the tetramantane carbon framework (secondary and tertiary carbons shown in FIGS. 22B-E). It will become apparent to the reader that one of the advantages of including diamondoid-containing pendant groups higher than adamantane are the vast number of possible attachment sites for hydrophilic-enhancing groups, alkyl groups, and polymerizable groups.

Etch Resistance

The inclusion of diamondoid-containing monomers higher than adamantane is contemplated to have the advantageous result of imparting enhanced etch resistance to the polymer. As discussed in a reference titled "Lithographic Resists," by W. D. Hinsberg et al. (IBM Research Division, K-Othmer, Encyclopedia of Chemical Technology), a parameter was devised by Ohnishi et al. to correlate a photoresist's chemical composition with its ability to withstand an etching environment. The parameter is given by $N/(N_c-N_o)$, where N is the total number of atoms in the polymer repeat unit, including hydrogen atoms, $N_c$ is the number of carbon atoms, and $N_o$ is the number of oxygen atoms.

The model serves as a fair predictor of etch rates for polymers under conditions where physical ion bombardment is a significant component, as is the case for reactive ion etching. The relation fails for low ion energy plasma conditions, such as those that what occurred in a downstream glow discharge process, where etching mechanisms are primarily chemical in nature. The Ohnishi parameter predicts that polymers having a high content of carbon (e.g., a low Ohnishi number) will exhibit low etch rates. In contrast, incorporation of hydrogen and/or oxygen into the repeat unit structure increases the etch rate, while an increased carbon content reduces the etch rate.

Figure 23:
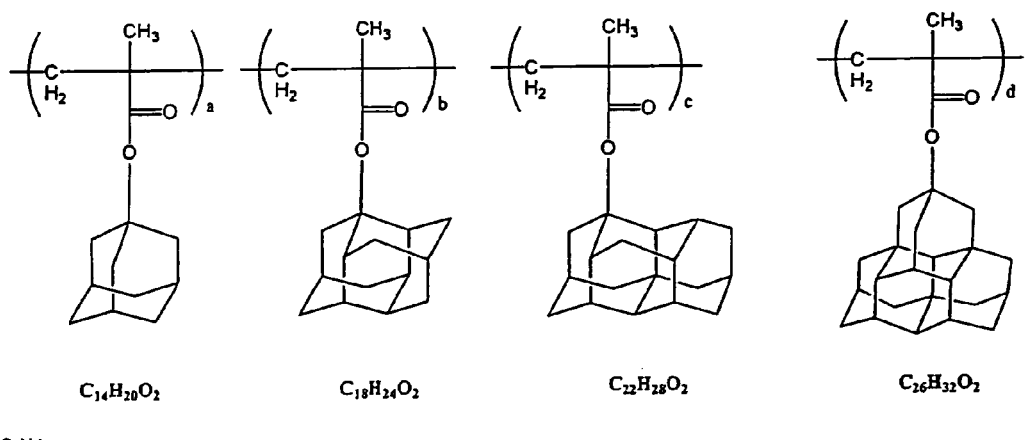
FIGS. 23A-B illustrate Ohnishi parameter calculations for base resin repeat units having adamantane, diamantane, triamantane, and iso-tetramantane pendant groups, and for the same pendant groups with 1, 2, 3, and 4 hydroxyl groups, respectively.
Figure 23:
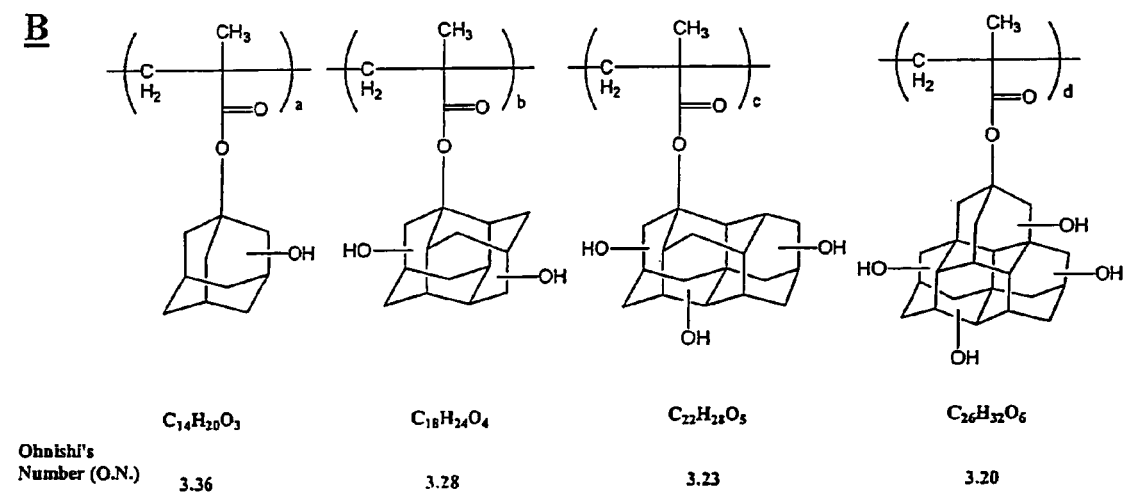

The Ohnishi numbers for exemplary monomers of the present invention, with adamantane for comparison, are shown with their respective schematic drawings in FIG. 23A. Referring to FIG. 23A, an adamantane-containing repeat unit has an Ohnishi number of 3.00, while this number decreases for diamantane, triamantane, and tetramane as follows: 2.75, 2.60, and 2.50. As taught by the present disclosure, however, it is necessary to include hydrophilic-enhancing groups as substituents on the diamondoid pendant groups, and the number of these hydrophilic-enhancing groups that are required will increase as the size of the diamondoid increases.

It is a surprising result just how many of these hydrophilic-enhancing groups may be tolerated with respect to etch resistance. For example, FIG. 23B calculates the Ohnishi number for the same series adamantane, diamantane, triamantane, and tetramantane, only an additional hydroxyl group is added as a substituent each time the size of the diamondoid is increased. Even with this additional "burden" on the etch resistance of the resist, the Ohnishi number still decreases for the series adamantane with one hydroxyl substitutent, diamantane with two hydroxyl substituents, triamantane with three hydroxyl substituents, and tetramantane with four hydroxyl substituents (3.36, 3.29, 3.24, and 3.20, respectively).

Multiple Acid-Labile Sites

Figure 24:
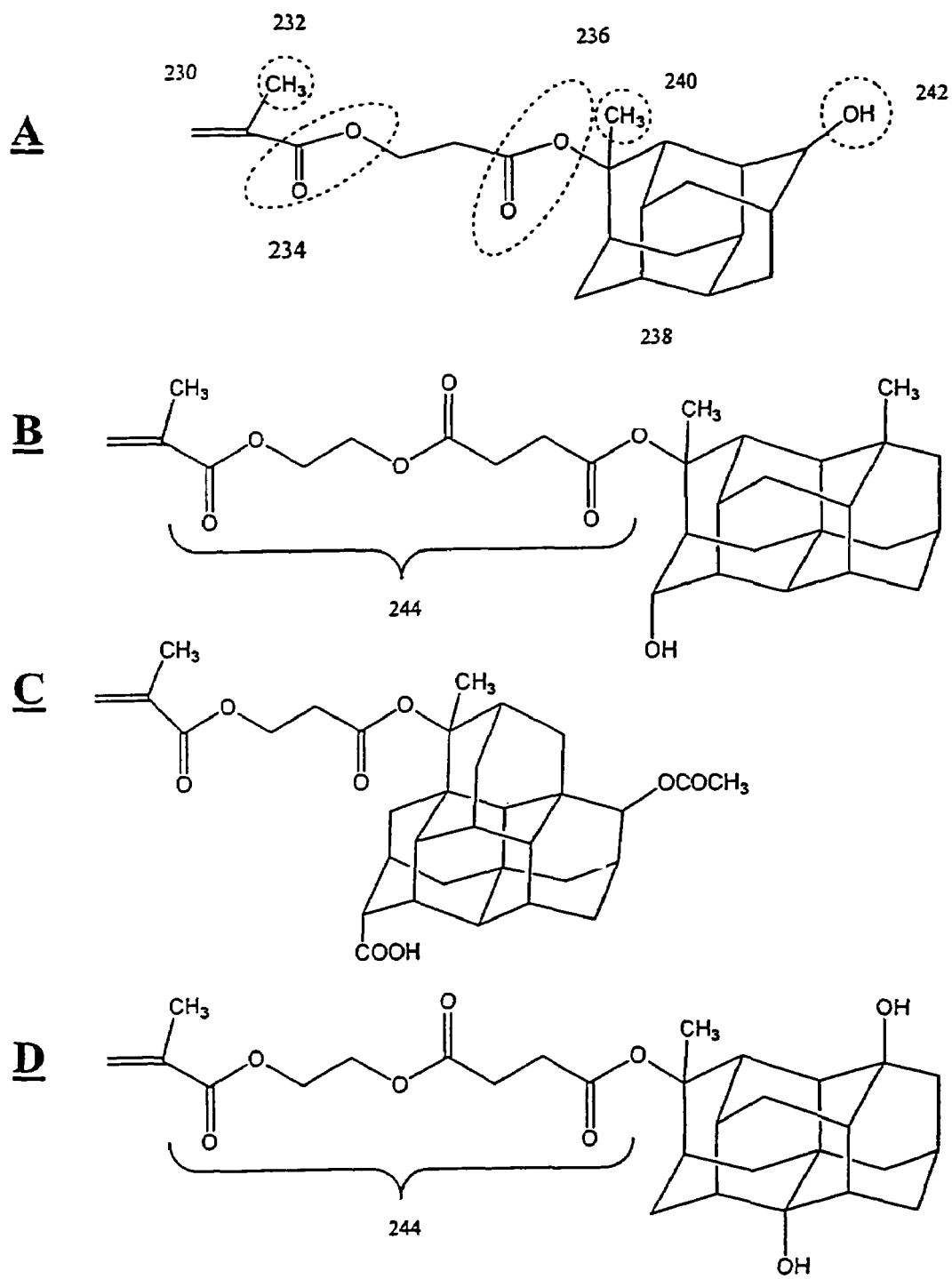
FIG. 24A-D shows exemplary diamondoid-containing monomers with multiple acid-labile sites.

Embodiments of the present invention include the ability of the diamondoid containing pendant group to be cleaved at multiple sites in the link connecting the pendant group to the main polymer chain. This is illustrated schematically in FIGS. 24A-D. Referring to FIG. 24A, a polymerizable group 230, which along with methyl group 232 and ester group 234 defines this exemplary polymer as a methacrylate, is attached through a second ester leakage 236 to diamondoid 238. The diamondoid 238 has an alkyl substituent 240 attached to the same carbon atom as the ester linkage 236. For exemplary purposes, a hydroxyl substituent 242 is shown attached to diamondoid 238, which in this case is a diamantane molecule.

The purpose of multiple ester linkages 234 and 236 is to provide a multiplicity of locations for the acid generated from the exposure event to cleave pendant diamondoid 238 from the main polymer chain (not shown). The advantages of providing multiple acid cleaving sites is at least twofold: 1) a weaker acid may be used to cleave the diamondoid pendant groups, allowing at the same time for a decreased post exposure bake temperature relative to what otherwise might have been necessary, and 2) a potentially larger variety of photo-acid generators become available. The ability to lower the post exposure bake temperature, to 110° C. or less, for example, is highly desirable in the industry because of uniformity considerations. Multiple acid-cleaving sites are contemplated to be effective for the purposes cited above because the acid-cleaving process is a diffusion driven one, and having more sites available means that the acid molecule does not have to diffuse as far.

Three more examples of diamondoid-containing monomers with multiple acid-labile sites are shown in FIGS. 24B, C, and D, wherein the diamondoid in FIG. 24B is a triamantane with a hydroxyl and methyl substituents, and the linking group 244 contains three ester linkages; the tetramantane in FIG. 24C has acetate and a carboxylic acid substituent groups (and two ester linkages), and the triamantane in FIG. 24D has two hydroxyl substituents (and three ester linkages).

Lactone-Containing Diamondoid Pendant Groups

Figure 25:
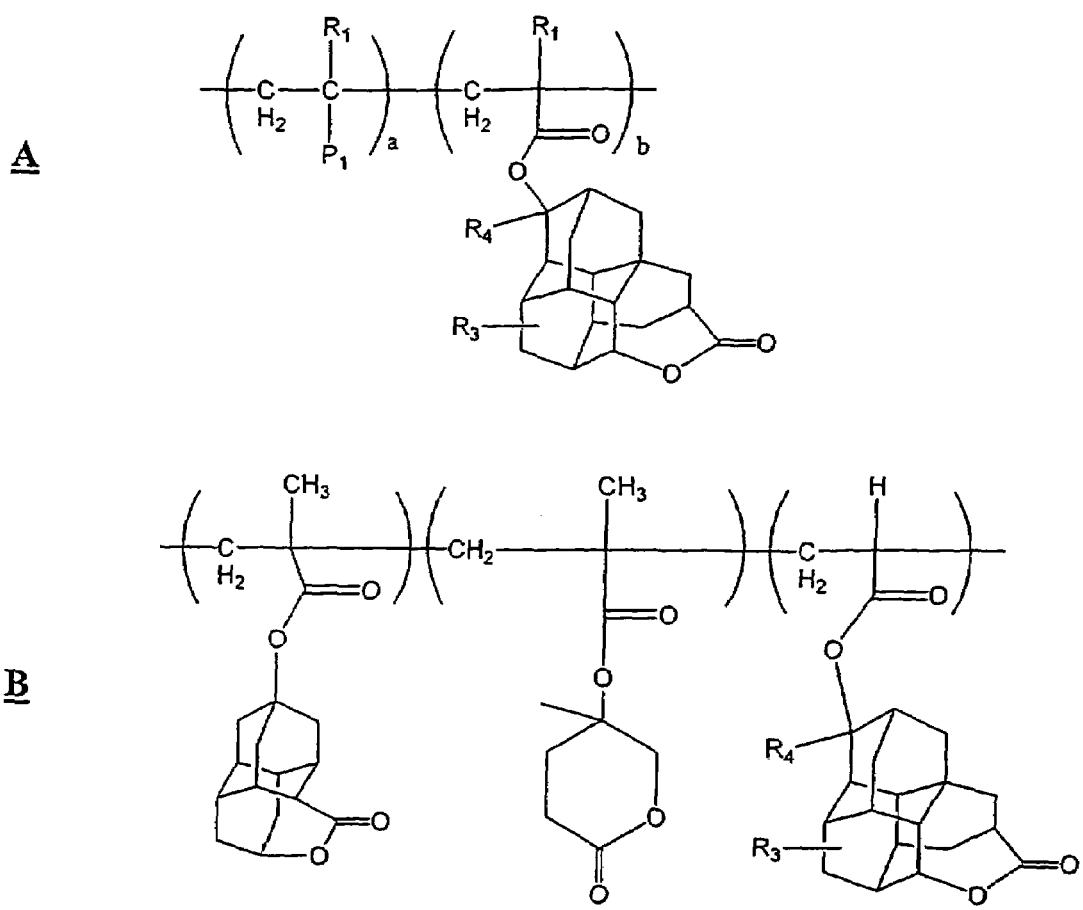
FIGS. 25A-B illustrate exemplary lactone-containing pendant groups, wherein the lactone group may be part of either the diamondoid-containing pendant group, or the non-diamondoid containing pendant group.
Figure 26:
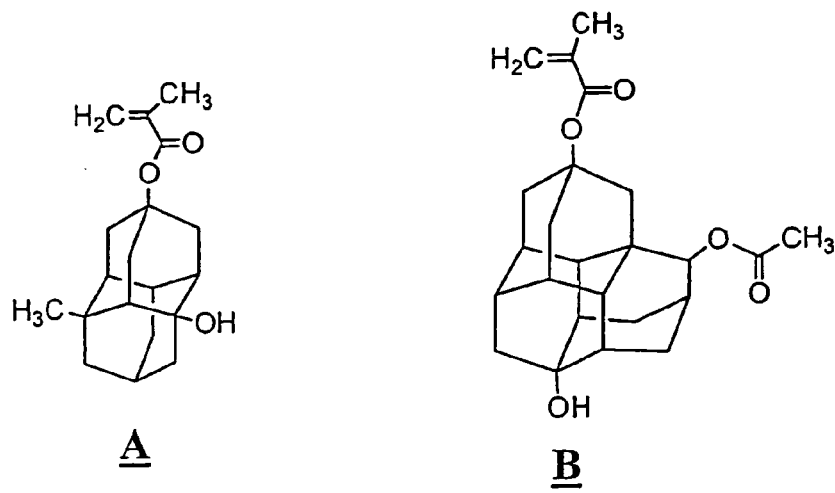
FIG. 26 illustrates an exemplary block co-polymer of the present invention.
Figure 26:
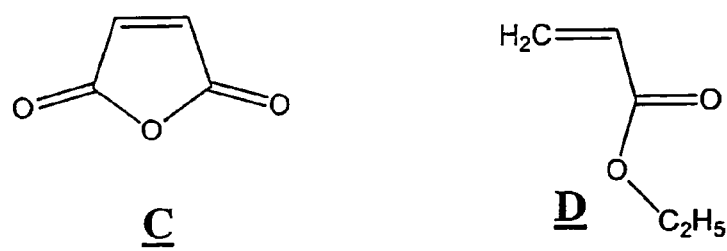
Figure 26:
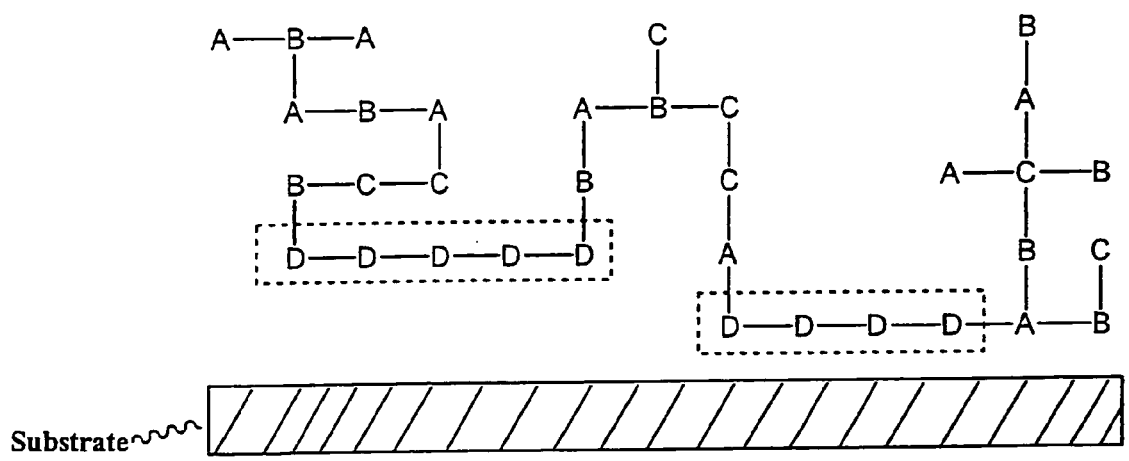
Figure 27:
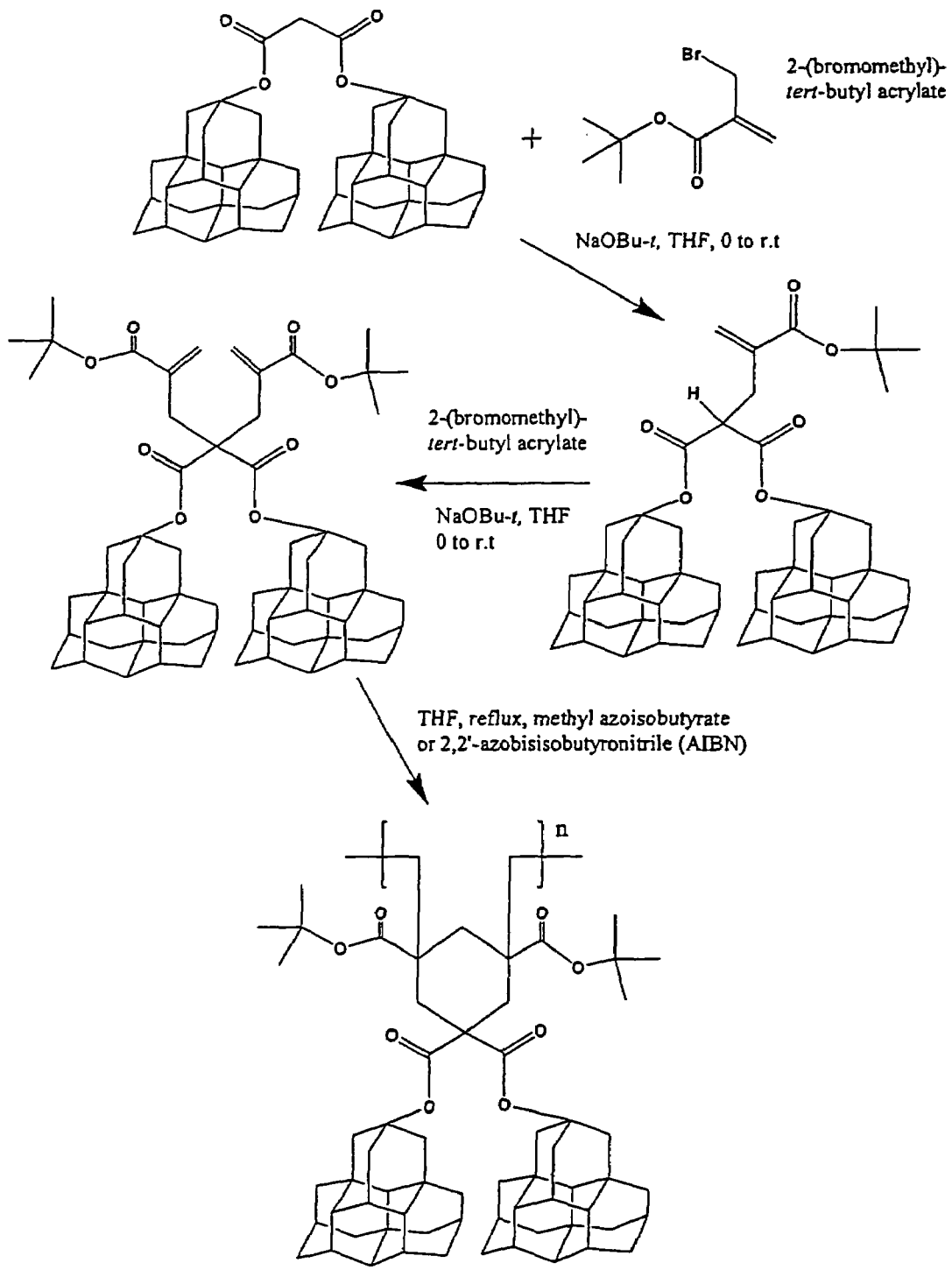
FIG. 27 illustrates a synthetic pathway for producing a polymer containing iso-tetramantane pendant groups.
Figure 28:
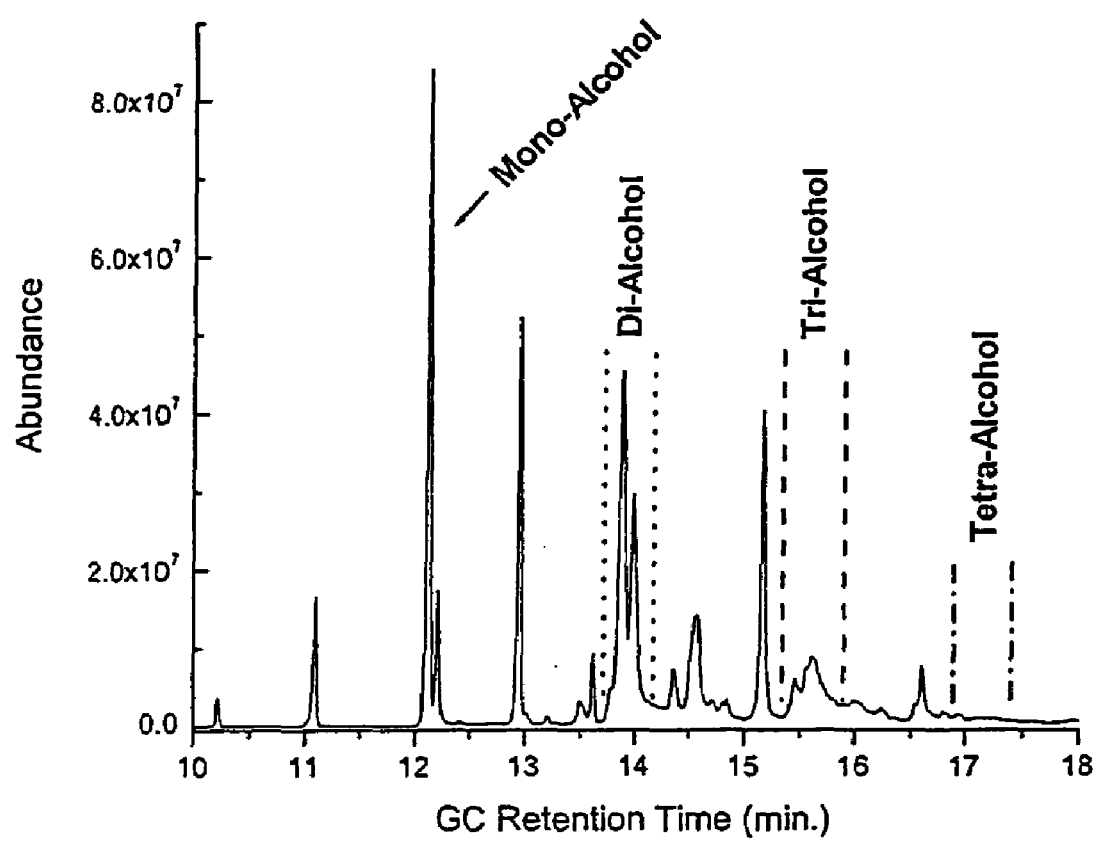
FIG. 28 shows the total ion chromatogram (TIC) of the resulting hydroxylation reaction mixture (10-18 min.)
Figure 29:
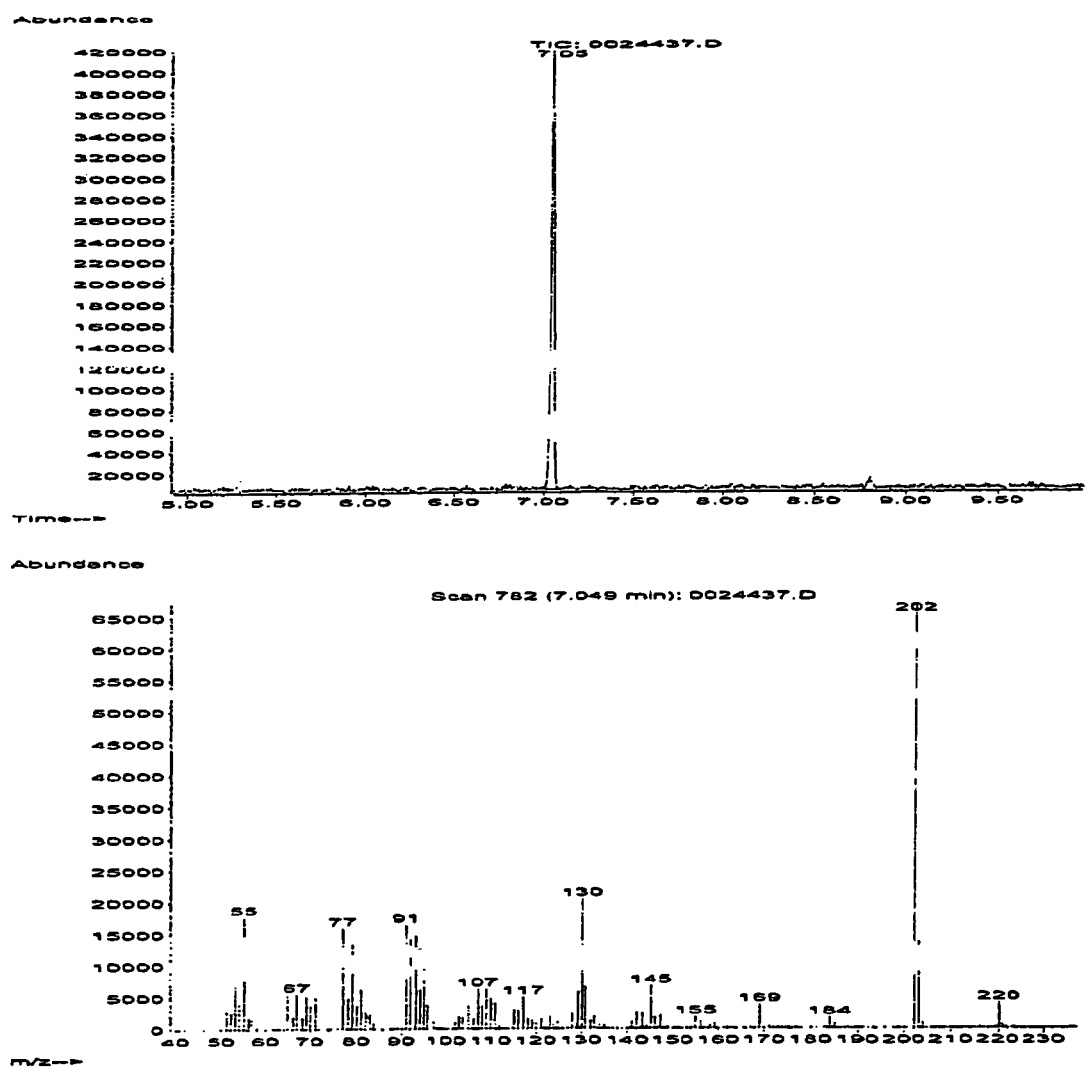
FIG. 29 shows the TIC of the separated di-hydroxylated diamantane with its corresponding mass spectrum.
Figure 30:
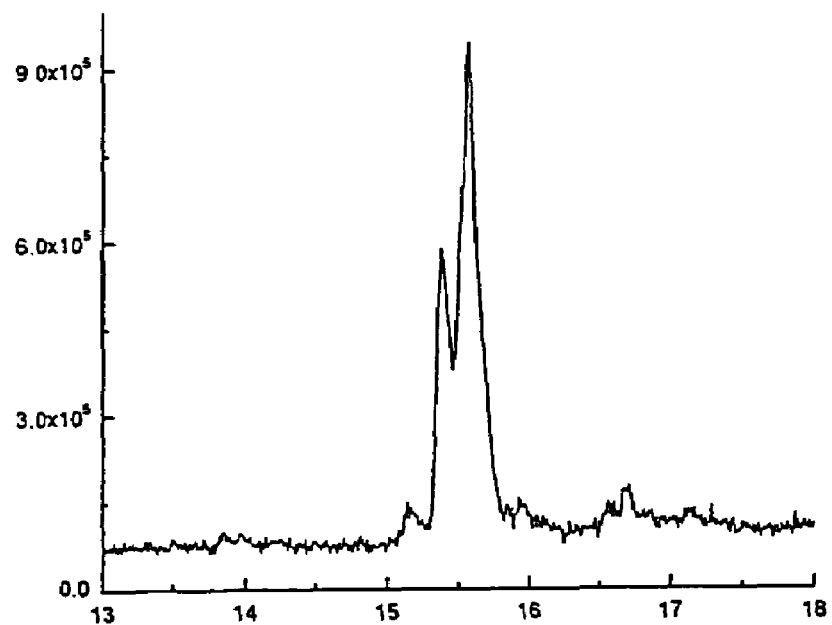
FIG. 30 shows the TIC of the separated tri-hydroxylated diamantane isomers with a mass spectrum of an isomer.
Figure 30:
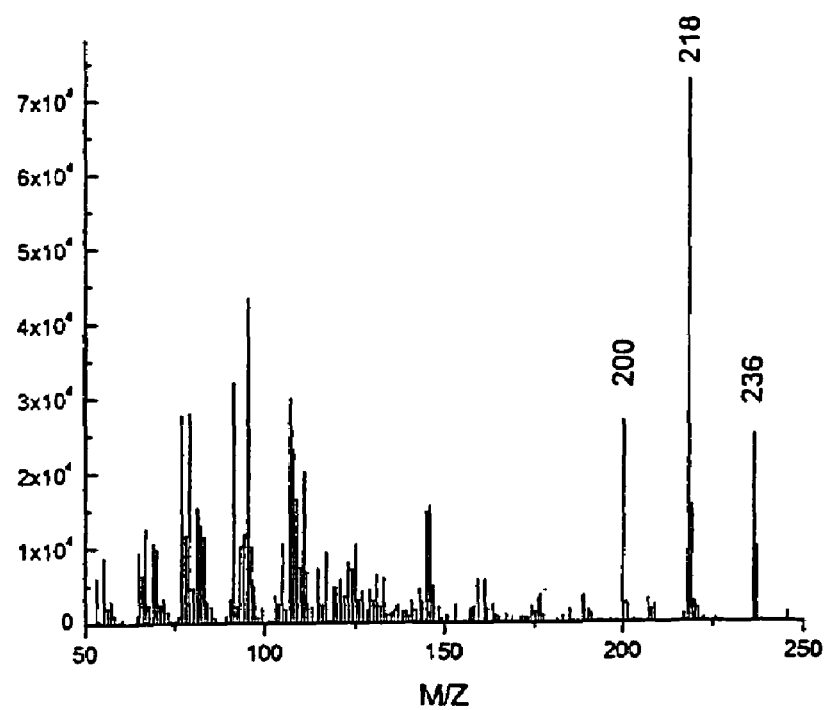
Figure 31:
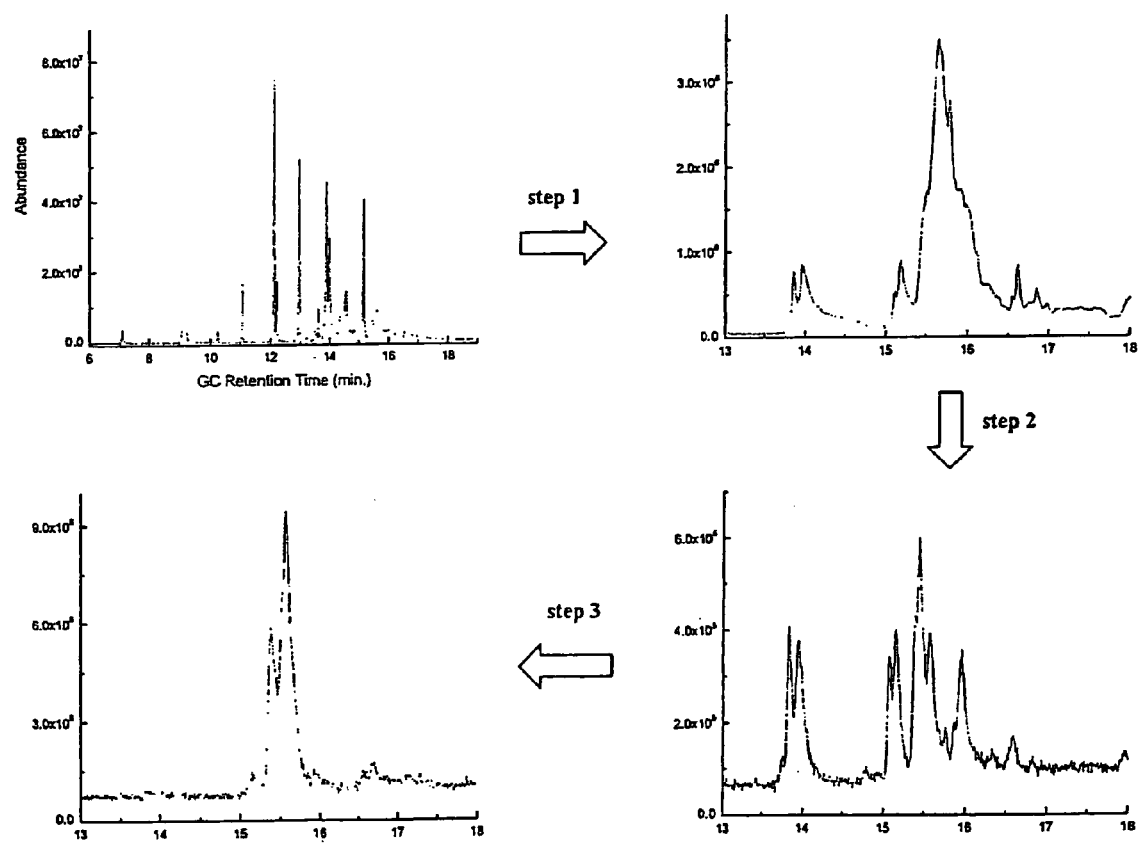
FIG. 31 shows a process to separate and purify the tri-hydroxylated diamantanes from the hydroxylation reaction mixture: step 1: water extraction; step 2: first flash column chromatography; step 3: second flash column chromatography. In one embodiment of the present invention, step 2 may be eliminated.
Figure 32:
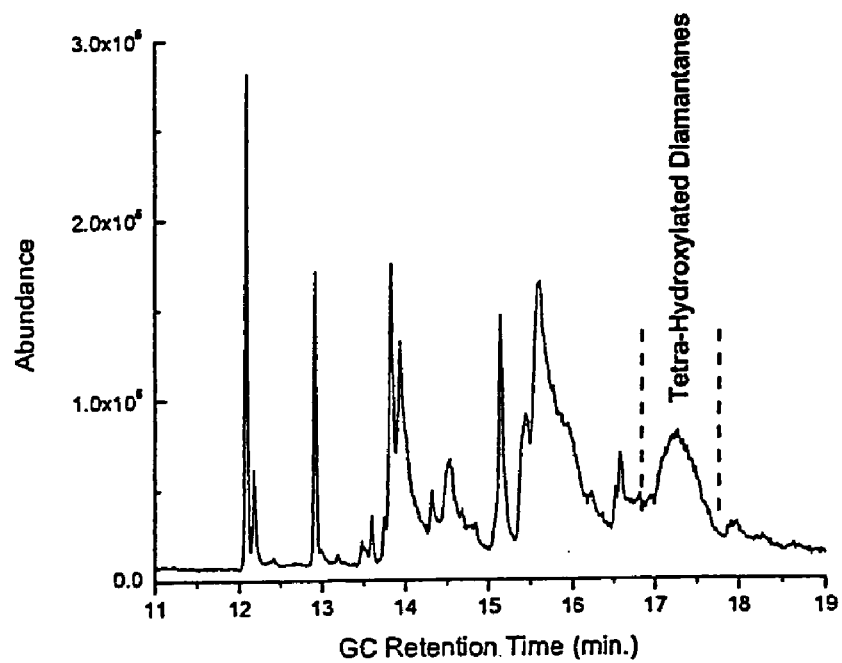
FIG. 32 shows the TIC of the precipitated solids from the hydroxylation reaction, and the mass spectrum at 17.27 minutes identifying the tetra-hydroxylated diamantanes.
Figure 32:
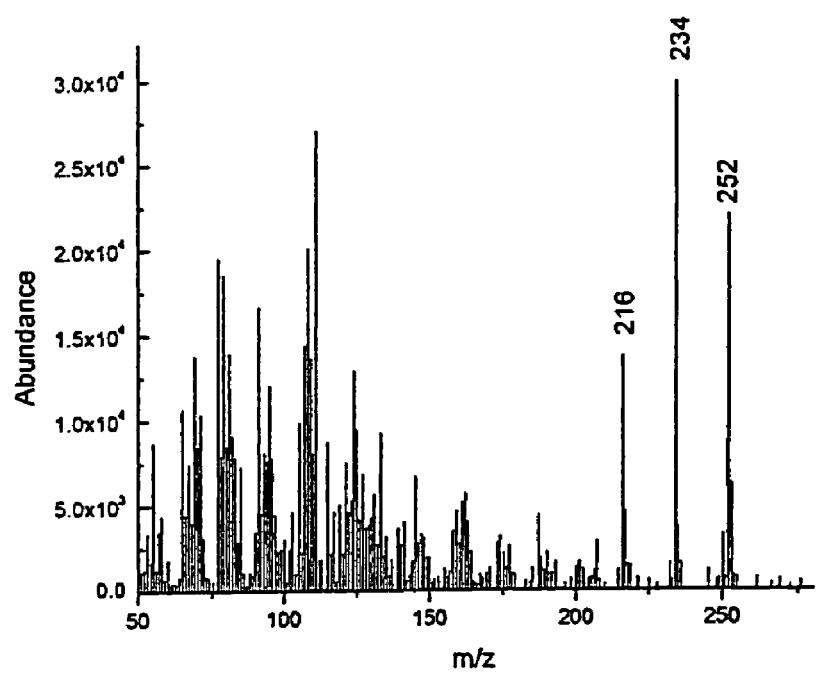
Figure 33A:
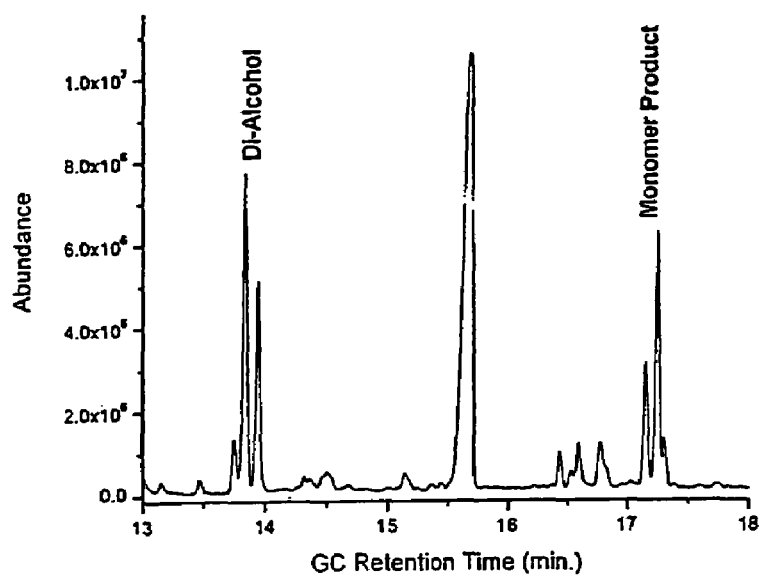
FIG. 33 shows the TIC of the esterification reaction mixtures (A from example 10 and B from example 11) between 13 and 18 minutes.
Figure 33B:
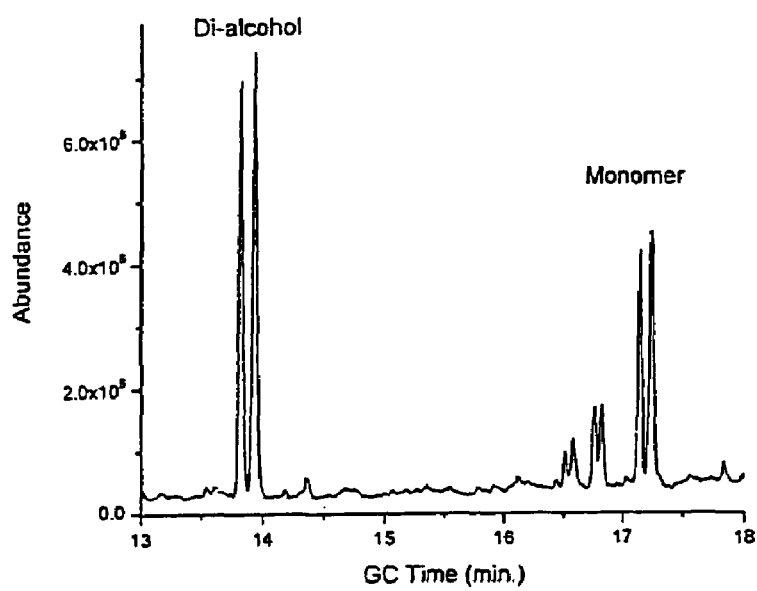
Figure 34:
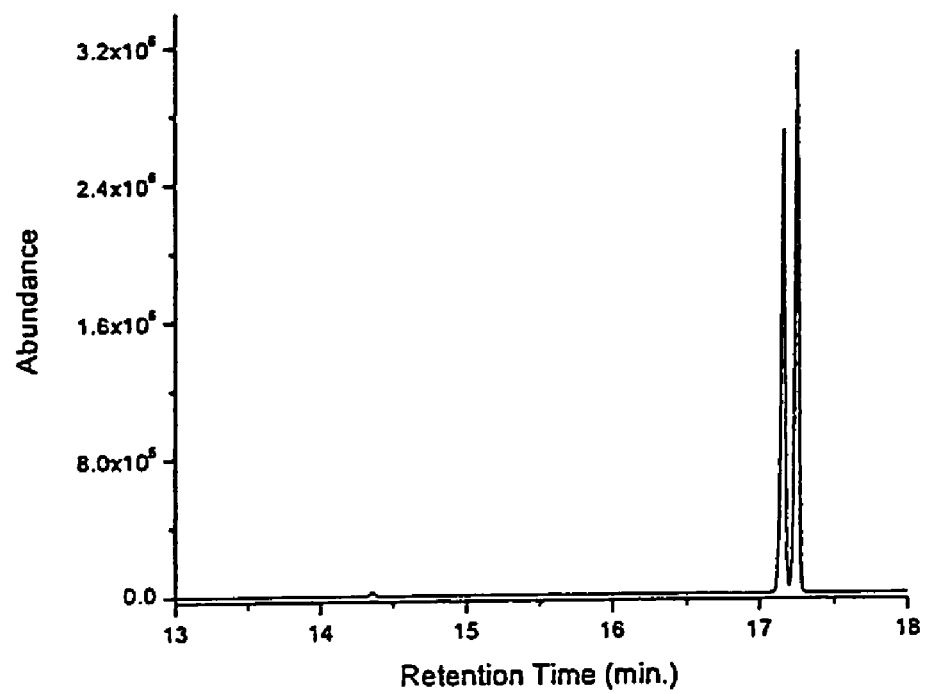
FIG. 34 shows the TIC of the separated mono-hydroxyl diamantane methacrylate isomers with a mass spectrum of one of the isomer.
Figure 34:
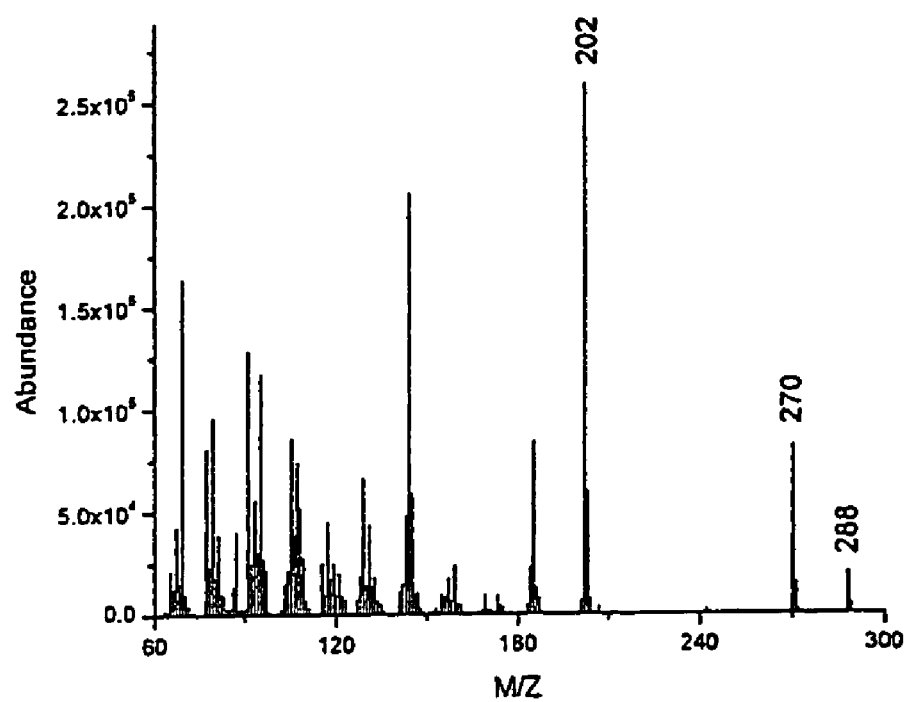

The adhesion enhancing lactone group need not be restricted to the non-diamondoid containing pendant group P1 of FIGS. 21A-B. An exemplary polymer containing lactone groups in both the non-diamondoid and the diamondoid-containing pendant groups is shown in FIGS. 25A-B.

Fully Formulated Resists

The photoresist composition may further include a solvent such as ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether (PGME), propylene glycol monomethyl ether acetate (PGMEA), ethylene carbonate, toluene, ethyl acetate, butyl acetate, methyl lactate, ethyl lactate, methyl methoxypropionate, ethyl ethoxypropionate, methyl methoxypropionate, ethyl pyruvate, propyl pyruvate, N,N-dimethylformamide, dimethylsulfoxide, N-methylpyrrolidone, and tetrahydrofuran.

The photoresist compositions of the present embodiments may be developed in an aqueous alkaline solution such as sodium hydroxide, potassium hydroxide, sodium carbonate, sodium silicate, sodium metasilicate, aqueous ammonia, a primary amind, ethylamine, n-propylamine, a secondary amine, diethylamine, di-n-butylamine, a tertiary amine, triethylamine, methyldiethylamine, an alcohol amine, dimethylethanolamine, triethanolamine, a quaternary ammonium salt, tetramethylammonium hydroxide, tetraethylammonium hydroxide, a cyclic amine, pyrrole, and piperidine.

The photoresist compositions of the present invention further include a photoacid generator selected from the group consisting of an onium salt, a diazonium salt, an ammonium salt, a phosphonium salt, an iodonium salt, a sulfonium salt, a selenonium salt, an arsonium salt, an organic halogeno compound, and an organo-metal/organic halide compound. The photoacid generator may have an o-nitorbenzyl type protecting group, and it may generate a sulfonic acid upon photolysis. Furthermore, the photoresist composition may contain the photo-acid generator in an amount ranging from about 0.01 to 30 weight percent.

The photoresist composition of the present embodiments may further include an additive selected from the group consisting of a surface active agent, an organic basic compound, an acid decomposable dissolution inhibiting compound, a dye, a plasticizer, a photosensitizer, and a compound promoting solubility in a developing solution, as well as diamondoid derivatives as an additive.

EXAMPLES

The present invention will be described in detail below in terms of example; however, the present invention is not limited in any way to these examples. The reaction mixture and the products were analyzed and characterized by gas chromatography/mass spectrometry (GC/MS) to confirm the presence of target compounds formed and the purity of the products separated. The GC/MS systems used is an HP 5890 Series II Chromatography connected to an HP 5973 Series MSD (mass selective detector).

Example 1

47.1 g of diamantane was dissolved in 375 ml of acetic acid, then 4.1 g of N-hydroxyphthalimide (NHPI), 0.322 g of Co(acac)$_2$ (cobalt (II) acetylacetonate) were added into the mixture. The mixture was stirred for about 23 hours at around 75° C. in a bubbling oxygen atmosphere. During the reaction, an additional portion of NHPI and Co(acac)$_2$ were added. After cooling down to room temperature (20° C.) and filtrating off the precipitated unreacted diamantane, the orange colored reaction mixture was concentrated under vacuum to give a dark red oily liquid. The dark red oily liquid was dissolved in methylene chloride. The methylene chloride solution of the reaction mixture was first extracted with water for several times. The combined water layers were then extracted with methylene chloride for a few times and finally the combined organic layers were concentrated and subjected to silica gel column chromatography, thus producing di-hydroxylated diamantane with yields of about 30%. The conversion rate of the diamantane was about 64%.

Example 2

A mixture of 9.42 g of diamantane, 0.82 g of N-hydroxyphthalimide (NHPI), 0.064 g of Co(acac)$_2$ (cobalt (II) acetylacetonate) and 75 ml of acetic acid was stirred for about 23 hours at around 75° C. in an oxygen bubbling atmosphere. During the reaction, an additional portion of NHPI and Co(acac)$_2$ were added. After cooling down to room temperature (20° C.), the reaction mixture was then concentrated and subjected to silica gel column chromatography, thus producing di- and tri-hydroxylated diamantane with yields of about 30% and 20% respectively.

Example 3

A mixture of 18.84 g of diamantane, 1.64 g of N-hydroxyphthalimide (NHPI), 0.129 g of Co(acac)$_2$ (cobalt (II) acetylacetonate) and 75 ml of acetic acid was stirred for about 23 hours at around 75° C. in a bubbling oxygen atmosphere. During the reaction; an additional portion of NHPI and Co(acac)$_2$ were added. The reaction mixture was concentrated and the concentrated reaction mixture was dissolved in methylene chloride. The methylene chloride solution of the reaction mixture was first extracted with water for several times. The combined water layers were then extracted with methylene chloride for a few times and finally the water was evaporated and the residual was subjected to flash silica gel column chromatography, thus producing tri-hydroxylated diamantine with yields of about 20%.

Example 4

12.4 g of the crude red oily liquid from water extractions in Example 1 mainly containing tri-hydroxylated diamantine was dissolved in about 200 mL ethyl alcohol. 27 g of activated carbon (60-100 mesh) was added into the ethyl alcohol solution. The mixture was then stirred for about 3.5 hours at room temperature (20 C). After filtration, the colorless solution was concentrated to give a colorless oily liquid.

Example 5

600 mL of combined methylene chloride extractions in Example 1 were added 6 g of activated carbon. The mixture was stirred for about 20 hours at room temperature (20° C.). After filtration, a pale yellow solution was obtained and the solvent evaporated to give a pale yellow solids. The crude solids were subjected to silica gel column chromatography, thus producing a colorless solid of di-hydroxylated diamantine.

Example 6

5 g of colorful oily liquid from the water extractions in Example 3 was dissolved in 70 mL of ethyl alcohol. Then 10 g of activated carbon was added and the mixture was stirred for about 3.5 hours at room temperature (20° C.). After filtration, the colorless solution was concentrated to an almost colorless oily liquid. The liquid was then dissolved in 2:1 v/v methylene chloride and THF (tetrahydrofuran). The solution was passed on a flash short silica gel column eluting first with 2:1 v/v methylene chloride and THF followed by THF and ethyl alcohol (5:1 v/v). The second fraction was concentrated to give a colorless oily liquid of tri-hydroxylated diamantane. The first fraction was concentrated to mainly give a white solid of di-hydroxylated diamantane.

Example 7

A portion of the dark red oily liquid in Example 1 was added a large excess amount of methylene chloride to precipitate a solid. After filtration and decoloring by activated carbon as above, the solids were analysized by GC/MS to show the presence of tetra-hydroxylated diamantane.

Example 8

Methacryloyl chloride was added dropwise to a stirred solution of an equimolar amount of di-hydroxylaed diamantine, excess triethylamine, and methylene chloride in a dry nitrogen atmosphere at around −30 to 0° C. Then the resulting mixture was further stirred for several hours while maintaining the temperature. The resultant mixture was filtrated, and the filtrate was concentrated under vacuum. The concentrated mixture was washed with water and brine. The water layers were combined and extracted with methylene chloride. The organic layers were combined and dried over anhydrous $Na_2SO_4$ and concentrated in vacuum. Finally, the concentrate was subjected to silica gel column chromatography, thus producing mono-hydroxyl diamantane methacrylate (yield: 5%). The conversion rate of the di-hydroxylated diamantane was about 10%.

Example 9

0.4 g of mono-hydroxylated diamantine was dissolved in 50 mL of methylene chloride. Methacryloyl chloride (0.2 mL) and triethylamine (0.5 mL) were added to the solution at room temperature (20° C.) under dry nitrogen atmosphere. The mixture was stirred at room temperature (20° C.) under dry nitrogen atmosphere for about 2 hours. Then the mixture was cooled down to 0° C. and another amount of methacryloyl chloride (0.15 mL) and 50 mg 4-DMAP (4-dimethylaminopyridine) in 5 mL cold methylene chloride were added into the mixture. The mixture was stirred at 0° C. for 30 minutes and then the cooling bath was removed. The mixture was again stirred at room temperature (20° C.) for 3 days. GC-MS of the reaction mixture showed the formation of diamantane methacrylate.

Example 10

To a 50 mL of methylene chloride were added the di-hydroxylated diamantane (5.73 mmol) and methacrylic acid (1.1 molar equ.). The mixture was stirred for 15 minutes at 0° C. under dry nitrogen. Dicyclohexyl carbodiimide (DCC, 2.1 molar equ.) and 4-DMAP (0.3 molar equ.) in about 25 mL cold methylene chloride were added, and the mixture was then stirred for 30 minutes at 0° C. under dry nitrogen. The cooling bath was then removed and the solution allowed to warm to room temperature (about 20 C). After being stirred for 50 hours under nitrogen, the reaction mixture was filtered through a fine glass frit to yield a clear filtrate and the insoluble urea byproduct as a fine white-grey solid. The clear filtrate was washed with water (3×50 mL), 5% acetic acid aqueous solution (3×20 mL), and finally again with water (3×30 mL). The organic layer was separated, dried over anhydrous $Na_2SO_4$, filtered, and the solvent evaporated. The residual was subjected to column chromatography to give mono-hydroxyl diamantane methacrylate (yield: 50%). The conversion rate of the di-hydroxylated diamantane was about 60%.

Example 11

5.8 mmol of di-hydroxylated diamantane, 6.4 mmol of triethylamine and 75 mL of methylene chloride were placed in a three necked round-bottom flask. A mixed solution of 5.5 mmol of methacryloyl chloride and 5 mL methylene chloride was added dropwise over a period of 5 minutes under stirring with the reaction temperature maintained at 0° C., and the mixture was future stirred for 3 hours at 0° C. under nitrogen. The cooling bath was then removed and the mixture was stirred at room temperature (20° C.) for 23 hours. At last the temperature was increased to about 30° C. and the mixture was stirred at the increased temperature for 2 more hours while adding 0.25 mL of the acid chloride and 0.5 mL of triethylamine. An extraction was performed by adding water to the reaction mixture, and the organic layer was separated, washed with water and brine. The water layer was extracted with methylene chloride. The organic layers were combined, dried with anhydrous $Na_2SO_4$ and concentrated in vacuum. The concentrate was subjected to silica gel column chromatography, thus producing mono-hydroxyl diamantane methacrylate (yield: 40%). The conversion rate of the di-hydroxylated diamantane was about 60%.

Many modifications of the exemplary embodiments of the invention disclosed above will readily occur to those skilled in the art. Accordingly, the invention is to be construed as including all structure and methods that fall within the scope of the appended claims.

What is claimed is:

1. A method of preparing hydroxylated diamantanes selected from the group consisting of di-hydroxylated diamantane, tri-hydroxylated diamantane, tetra-hydroxylated diamantanes, and mixtures thereof, the method comprising the steps of:
   a) reacting diamantane with N-hydroxyphthalimide (NHPI) and Co(acac)$_2$ (cobalt (II) acetylacetonate) in a reaction mixture;

b) concentrating the reaction mixture to form a concentrated product; and c) recovering hydroxylated diamantanes from the concentrated product.

2. The method of claim 1, further comprising the step of adding additional portions of N-hydroxyphthalimide (NHPI) and Co(acac)$_2$ (cobalt (II) acetylacetonate) to the reaction mixture during step a).

3. The method of claim 1, further comprising the step of dissolving the concentrated product in a solvent, and then extracting the resulting solution with water to form a water layer and a solvent layer.

4. The method of claim 3, further comprising the step of subjecting the solvent layer to silica gel column chromatography to recover di-hydroxylated diamantanes.

5. The method of claim 3, wherein the solvent is methylene chloride.

6. The method of claim 3, further comprising the steps of dissolving the water layer in ethyl alcohol to form an ethyl alcohol solution, adding activated carbon to the ethyl alcohol solution, and then recovering tri-hydroxylated diamantanes from the activated carbon and ethyl alcohol solution.

7. The method of claim 3, further comprising the steps of:

a) dissolving the water layer in ethyl alcohol to form an ethyl alcohol solution;

b) adding activated carbon to the ethyl alcohol solution of step a);

c) concentrating the activated carbon and ethyl alcohol solution of step b) to a concentrated product;

d) dissolving the concentrated product of step c) in methylene chloride and tetrahydrofuran; and e) passing the dissolved concentrated product of step d) through a silica gel column to elute a methylene chloride and tetrahydrofuran fraction and a tetrahydrofuran and ethyl alcohol fraction.

8. The method of claim 7, further comprising the step of recovering di-hydroxylated diamantanes from the methylene chloride and tetrahydrofuran fraction.

9. The method of claim 7, further comprising the step of recovering tri-hydroxylated diamantanes from the tetrahydrofuran and ethyl alcohol fraction.

10. The method of claim 1, further comprising the steps of dissolving the concentrated product in a large excess of methylene chloride to precipitate a solid, and then recovering tetra-hydroxylated diamantane as the precipitated solid.

* * * * *